(12) United States Patent
Shikinami

(10) Patent No.: US 6,281,262 B1
(45) Date of Patent: Aug. 28, 2001

(54) SHAPE-MEMORY, BIODEGRADABLE AND ABSORBABLE MATERIAL

(75) Inventor: Yasuo Shikinami, Osaka (JP)

(73) Assignee: Takiron Co., Ltd., Osaka (JP)

( * ) Notice: Subject to any disclaimer, the term of this patent is extended or adjusted under 35 U.S.C. 154(b) by 0 days.

(21) Appl. No.: 09/189,973

(22) Filed: Nov. 12, 1998

(51) Int. Cl.$^7$ .............................. A61L 17/12; A61L 27/16; C08F 283/14; C08G 63/08; C08L 67/04

(52) U.S. Cl. ..................... 523/105; 523/113; 523/115; 523/128; 525/450; 604/530; 623/22; 623/926; 264/230

(58) Field of Search ..................... 523/105, 113, 523/115, 128; 524/600; 525/450; 623/22, 926; 264/230; 604/530

(56) References Cited

U.S. PATENT DOCUMENTS

| | | | |
|---|---|---|---|
| 4,916,207 | * | 4/1990 | Boyle, Jr. et al. ................. 523/113 |
| 4,950,258 | * | 8/1990 | Kawai et al. ....................... 264/230 |

FOREIGN PATENT DOCUMENTS

| | | |
|---|---|---|
| 0 326 426 A2 | 8/1989 | (EP) . |
| 0 475 077 A3 | 3/1992 | (EP) . |
| 94/28070 | * 12/1994 | (WO) . |

\* cited by examiner

*Primary Examiner*—Peter Szekely
(74) *Attorney, Agent, or Firm*—Sughrue, Mion, Zinn, Macpeak & Seas, PLLC

(57) ABSTRACT

Shape-memory biodegradable and absorbable materials which make it possible to easily treat vital tissues by suture, anastomosis, ligation, fixation, reconstitution, prosthesis, etc. without causing burn. These materials never induce halation in MRI or CT and never remain in vivo. Such a shape-memory biodegradable and absorbable material is a material made of a molded article of lactic acid-based polymer and can be recovered to the original shape without applying any external force thereto but heating to a definite temperature or above. It is obtained by deforming a molded article (a primary molded article) made of a lactic acid-based polymer and having a definite shape into another molded article (a secondary molded article) having another shape at a temperature higher than the glass transition temperature thereof but lower than the crystallization temperature thereof (or 100° C. when the molded article has no crystallization temperature) and then fixing said molded article to the thus deformed shape by cooling it as such to a temperature lower than the glass transition temperature. When this material is heated to the above-mentioned deformation temperature or above, it is immediately recovered to the original shape. The lactic acid-based polymer is hydrolyzed and absorbed in vivo.

47 Claims, 14 Drawing Sheets

SHAPE-MEMORY, BIODEGRADABLE AND ABSORBABLE MATERIAL

FIELD OF THE INVENTION

This invention relates to shape-memory biodegradable and absorbable materials which can be recovered to the original shape by reheating and degraded and absorbed in vivo.

BACKGROUND OF THE INVENTION

Materials to be embedded in living bodies (i.e., implant materials) include metals, bioceramics, polymers, those with biological origins and hybrid materials.

These materials may be classified into so-called absorbable ones which are gradually absorbed and discharged from the body after exerting the functions in vivo and non-absorbable ones which cannot be degraded but substantially remain as such in vivo.

When these non-absorbable materials (synthetic materials) are kept in vivo over a long time, it is feared that these foreign matters undergoes some undesirable reactions due to the differences in physical or chemical (physiological) properties from biological constituents or the expression of toxicity caused by corrosion. Therefore, these materials are sometimes taken out from the body, if possible, by reoperative surgery. In such a case, a patient should be burdened with repeated pains and an additional fee. To relieve this situation, it has been required to develop biological materials which can be used as substitutes for the existing ones without resorting to any reoperative surgery.

Although biodegradable and absorbable materials are expected as useful in satisfying the above requirement, there are not such a great variety of absorbable materials as being usable as substitutes for all of nonabsorbable implant materials made of metals, ceramics, polymers, etc. Thus, research and development have been made to obtain a substitute for each of these existing materials.

Operative suture yarns and metallic materials (stainless steel, titanium, silver, platinum) employed for ligating missing or amputated parts are biomaterials which remain in the body after the completion of the operation. Suture yarns should be selected by considering tissue disorder, tissue tension, the occurrence of suture complication, effects of bodily fluids on the threads, infection, etc.

In general, silk yarns are employed in ligating fasciae and peritonea, nylon yarns are employed in ligating skin and nerves, polyester yarns are employed in fixing heart and tendons, while polypropylene yarns are employed in anastomosing nerves and blood vessels. Synthetic absorbable suture yarns (polyglycolic acid-based type) are used not only in the above sites but also in digestive tracts, etc.

In sites where a high strength is needed, on the other hand, use is made of metal wires made of stainless steel, titanium, etc. However, use of these metallic materials brings about troubles in image diagnosis. That is to say, light reflected thereby causes halation in magnetic resonance images (MRI) or computer tomography (CT) which have been rapidly spread in recent years as means for monitoring the conditions of patients under operation or postoperative healing state. Thus, it has been required to develop novel materials for suture, anastomosis or ligation which are usable as substitutes for metal wires.

As described above, various suture yarns are selected in operations to suit the occasion. In many cases, these yarns are employed in stanching, suturing or anastomosing various sites other than the main incised part. However, it sometimes takes the greater part of time to perform these treatments. Under these circumstances, it has been required to develop materials for suturing, anastomosing and ligating with which these treatments can be carried out more easily.

For example,. an incised tendon is fixed by suturing with a yarn. However, the procedure therefor has been becoming more and more complicated and it is therefore needed to develop fixation materials and convenient methods therefor. In operations in the thoracic or abdominal cavity, it is frequently observed that more than 50 blood vessels are incised. In such a case, it is necessary to perform suture and ligation at least 100 times for stanching and postoperative fixation. Therefore, it has been required to develop methods and materials by which these procedures can be carried out more easily. In addition, it is a practice to leave the conventional nonabsorbable materials as such in the body, since bypasses can be spontaneously formed after ligating blood vessels. Further, it is troublesome and risky to open-out the body again to take out metal clips, staples or various suture yarns therefrom, and there arises a dilemma that the body once opened-out should be sutured again. Accordingly, it is ideal that the materials to be used for the above purposes are biomaterials which can be degraded and absorbed in vivo and then discharged from the body, since the above-mentioned problems can be avoided by using these materials.

To achieve the above object, attempts have been made to produce staples and clips made of biodegradable and absorbable polymers (polyglycolic acid, polylactic acid, glycolic acid/lactic acid copolymer, polydioxanone, etc.) which have been molded into particular shapes designed by taking the physical strength of the polymers into consideration and can be physically caulked by using particular instruments. These products are used in operations in practice. However, these products still suffer from some disadvantages. Namely, they are troublesome in handling. In addition, they should be considerably larger in size than metallic ones because of the poor physical strength thereof. Moreover, they cannot be fastened tightly, since they are inferior in ductility to metals.

SUMMARY OF THE INVENTION

The present invention, which has been completed in order to satisfy the above requirements, aims at developing shape-memory biodegradable and absorbable implant materials made of novel biodegradable and absorbable materials which are hydrolyzed and absorbed in vivo when allowed to stand therein. These biodegradable and absorbable materials are usable as medical prosthetic appliances, fillers or scaffolds. Moreover, they make it possible to easily and surely perform anastomosis, ligation, suture, fixation, fixation, etc., for example, ligating or anastomosing incised blood vessels (stanching), suturing incised sites, fixing incised tendons and fixing and fixing fractured bones. When employed in MRI or CT, they cause no halation. They are further useful as base materials in controlled drug-release or tissue engineering.

As shape-memory materials, there have been developed synthetic polymers (norbornane-based one, trans-polyisoprene, styrene/butadiene copolymer, polyolefin, polyester, polyurethane, polyacryl, etc.) and natural polymers (cellulose fiber, protein fiber, etc.). However, none of them is biodegradable and absorbable in vivo. That is to say, it has never been reported hitherto that a biodegradable and absorbable material recognized as a biocompatible material is processed into a shape-memory material and embedded in vivo in practice, as done in the present invention.

The fundamental shape-memory biodegradable and absorbable material of the present invention, by which the above-mentioned objects have been achieved, is made of amolded article of a lactic acid-based polymer wherein said material can be recovered to the original shape without applying any external force thereto but by heating to a definite temperature or above. Namely, a molded article made of a lactic acid-based polymer in a definite shape is deformed into another molded article at a temperature (Tf) higher than the glass transition temperature (Tg) thereof but lower than the crystallization temperature (Tc) thereof (or 100° C. when the molded article has no crystallization temperature) and then fixing said molded article to the thus deformed shape by cooling it as such to a temperature lower than the glass transition temperature (Tg), wherein said molded article can be recovered to the former molded article of the original shape by heating it again to said deformation temperature (Tf) or above.

Figure 1:
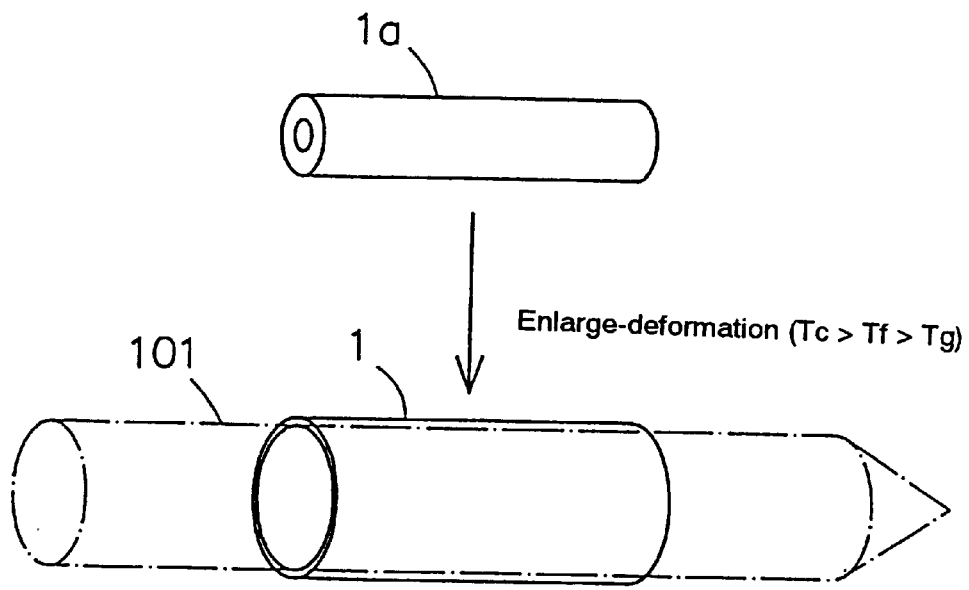
FIG. 1 is a diagram which illustrates a shape-memory material for vascular anastomosis according to an embodiment of the present invention.

In these drawings, each symbol has the meaning as defined below:

1, 2, 3: shape-memory material for vascular anastomosis;

21a: crimpy inner face;

4,5: shape-memory material for vascular ligation;

6 : shape-memory material for tendon fixation;

61: cut and lifted portion;

7, 70: shape-memory material for suture;

71: hook;

8, 10: shape-memory material for bone fixation;

9: shape-memory material for fixing bone plate for fracture fixation;

10a: cylinder;

10b: arm;

11: shape-memory material for preventing bone cement from leakage;

11a: cylindrical plug;

11b: petal-like projection;

12: shape-memory material for preventing vascular reconstriction;

12b: pore;

13: shape-memory material for artificial hip joint; and 1a, 2a, 3a, 4a, 5a, 6a, 7a, 8a, 10c, 11c, 12a, 13a, 70a original shape.

DETAILED DESCRIPTION OF THE INVENTION

The term "deforming" as used herein involves any treatments and procedures for altering the shape of molded articles, for example, enlargement, drawing, compression, bending, twisting and combinations thereof.

In general, a polymer molecular aggregate having a shape-memory function has a structure consisting of a fixed phase having a function of controlling the fluidity of the polymer molecules so as to fix the material to the shape of a molded article, and a reversible phase in which the polymer molecules can be softened and hardened repeatedly via fluidization/solidification with a change in temperature above or below a definite point.

The formation of the fixing phase depends on some chemical factors such as the interaction systems among individual linear polymer molecular chains, the density and form of the interactions, interlocking of molecular chains, etc.

The interactions among polymer molecular chains can be divided into those due to strong primary bonds (covalent bond, coordinate bond, ionic bond, etc.) and those due to relatively weak secondary binding forces (Coulomb forces, hydrogen bond, van der Waals force, etc.). The constrained phase (fixed phase) and the fluidized phase (reversible phase) are formed depending on the intermolecular actions the type of which is determined by the properties (for example, chemical structure, arrangement and steric specificity) of the monomers constituting the polymer. Owing to a difference in the interaction (binding force) among the polymer molecular chains, the polymer forms a rubber phase, a glass phase or a crystalline phase. Some polymers consist of one of these phases alone, while others comprise two or more thereof.

A shape-memory polymer shows a large change in modulus of elasticity at the glass transition temperature (Tg). The shape-memory function can be achieved by taking advantage of this characteristic. Namely, a molded article (the primary molded article) to which a definite shape (the original shape) has been imparted by a common method for molding plastics is softened by heating to a temperature (Tf) higher than the Tg of the polymer but lower than the melting temperature (Tm) thereof so as to deform it into a different shape. Next, the molded article is cooled to a temperature lower than Tg while maintaining the thus deformed shape (the secondary molded article). When it is heated again to a temperature higher than the secondary-molding temperature (Tf) but lower than Tm, the shape of the secondary molded article disappears and thus the article is recovered to the original shape of the primary molded article. The term "shape-memory polymer" means such a polymer which can be deformed into a secondary shape tentatively and then recovered to the original shape via the above-mentioned process.

The most effective polymers which can be recovered to the original shape include glassy polymers showing a large change in modulus of elasticity at the glass transition temperature (Tg). In these polymer, namely, the disappearance of the secondary shape and the recovery to the original shape can be performed efficiently and almost completely. Many of the lactic acid-based polymers to be used in the present invention show changes in modulus of elasticity (E') by 150-fold or above at Tg and, therefore, are appropriate as shape-memory materials.

The above-mentioned properties cannot be achieved by polymers consisting exclusively of fluidized phases, for example, those wherein the reversible phase is a rubber phase having a fluidity higher than that of the glass phase. In contrast thereto, polymers having a rubber phase alone with intermolecular-crosslinked moieties or consisting of two or more phases wherein a glass phase, a crystalline phase, etc. are mixed with a rubber phase exhibit the shape-memory and recovery functions. However, it might be still doubtful whether or not the secondary shape can be exactly fixed, the molded article can be completely recovered to the original shape and the shape-memory function and the recovery temperature are acceptable from the viewpoint of clinical use.

On the contrary, a crystalline phase serves as a fixed phase and no polymer consisting exclusively of this phase can exhibit any shape-memory function. There are some polymers comprising polymer molecular aggregates consisting of a crystalline phase and a rubber phase (in particular, a partly crosslinked rubber phase) at ordinary temperature or polymer molecular aggregates consisting of a crystalline phase and a glass phase mixed together which achieve the shape-memory function.

Among biodegradable and bioabsorbable polymers, some poly(a-oxy acid)s may be cited as typical examples of polymers which are excellent in biocompatibility and safety and have been accepted as implant materials to be used in vivo in practice. Polyglycolic acid is a polymer having Tm (melting temperature) of 230° C. (225–235° C.) and Tg of 36° C. (45–50° C.), while poly-L-lactic acid is a crystalline polymer (i.e., one having crystallization temperature) with Tm of 189° C. (195° C.) and Tg of 56° C. (55–65° C.), provided that the data given in parentheses are those reported in different documents.

These polymers fundamentally consist of a crystalline phase and an amorphous phase (a glass phase). Although they can be made completely amorphous by thermally treating in a specific manner, it is unavoidable that such a polymer is once converted into a crystalline polymer partly containing an amorphous glass phase in the process of molding (deforming) wherein it is fluidized by heating so as to enable molding. This is caused by the chemical structure of the monomers comprising a single isomer which are the constituting units of the polymer. Since this phenomenon is an unavoidable one, these polymers essentially fall within the category of crystalline polymers.

Although polyglycolic acid and polylactic acid, which are both homopolymers, are essentially crystalline polymers, they are each substantially composed of a crystalline phase and a glass phase. Accordingly, they can achieve the shape-memory function when deformed into the above-mentioned secondary shape at a temperature higher than Tg but lower than the crystallization temperature (Tc, Tc<Tm) and then solidified by cooling, though they each has a somewhat high Tg. In this treatment, however, the deformation should be performed at a high temperature of, for example, 100° C. or above, since these polymers contain a crystalline phase. Moreover, there arise additional problems such that the degree of crystallization is elevated during the treatment and thus the shape recovery should be carried out at a high temperature of 100° C. or above or the shape cannot be recovered completely to the original one. By taking these problems into consideration, it seems impossible to conclude that these polymers are usable as shape-memory polymers for practical use, in particular, as medical implants.

Lactic acid occurs as optical isomers, i.e., S(L)-lactic acid and R(D)-lactic acid. In usual, polylactic acid is obtained by preparing oligomers of these isomers, cyclized these oligomers to give dimers (lactide) and then further ring-opening polymerizing these dimers. The above-mentioned poly-L-lactic acid or poly-D-lactic acid made of the L-isomer or the D-isomer alone respectively is an essentially crystalline polymer owing to the steric specificity and molecular chains therein are in the state of an α-helix structure.

Cyclized lactic acid dimers are classified into three types, namely, one made of two L-isomer molecules, one made of two D-isomer molecules and one made of an L-isomer molecule and a D-isomer molecule (i.e., the meso-type), though these different isomers in the third type can be hardly extracted and separated from each other in practice. These dimers are called respectively L-lactide, D-lactide and DL(meso)-lactide. Poly-D,L-lactide (poly-D,L-lactic acid) can be synthesized by mixing L-lactide with D-lactide at a definite ratio followed by ring-opening polymerization. When the mixing ratio is 50/50 (by mol), the obtained polymer made of the D- and L-isomers is usually called poly-D,L-lactic acid. However, those prepared by using different mixing ratios are also referred to as poly-D,L-lactic acid in a broad sense.

When the content of the D-lactide differs from that of L-lactide, the major one serves as the key factor in the formation of block segments connected to each other. The shortest monomer connection unit of poly-D,L-lactide wherein L-lactide and D-lactide are bonded at an equimolar ratio is -(L-L-D-D)-. This shortest connection unit of the optical isomers results in properly disordered interaction among polymer molecular chains. As a result, these units can form no crystalline polymer, as in the case of polymers consisting of the L- or D-isomer alone, but a substantially amorphous glassy polymer at ordinary temperature. These units form no rubbery polymer because of the appropriate balance between the polarity and nonporality of the chemical structure of the lactic acid monomer. Poly-D, L-lactic acid with a molar mixing ratio of the D-isomer to the L-isomer of 50/50 has a Tg of 57° C. (55–60° C.).

The present inventors have paid their attention to the chemical structure, arrangement, phase structure, Tg, various physical properties, biodegradability and bioabsorbability of the above-mentioned poly-D, L-lactic acid and proved its efficacy as a shape-memory biodegradable and absorbable material. As a result, they have completed the present invention aiming at providing practically usable implant materials which can be embedded in vivo.

The present invention has been completed based on the recognition and understanding of the following facts. That is, a molded article made of poly-D, L-lactic acid as the fundamental component consists of a structural part capable of controlling the fluidity of the polymer and thus fixing the molded article to a definite shape (i.e., a fixed phase) and another structural part undergoing hardening and softening repeatedly with changes in temperature above or below the glass transition temperature (Tg) of the polymer (i.e., a reversible phase). When the original material is melt-molded into a definite shape and then cooled to Tg or below, the fixed and reversible phases are both fixed so as to maintain the shape of the primary molded article (i.e., the original shape). When this primary molded article is deformed by heating it again to a temperature (Tf) higher than Tg but lower than Tc, the reversible phase alone is fluidized to thereby form another molded article of a different shape. Then the molded article is cooled as such to Tg or below. As a result, the reversible phase is fixed and another molded article (i.e., the secondary molded article) differing in shape from the primary one can be obtained. When this secondary molded article is heated again to a temperature higher than Tf but lower than Tc, the reversible phase is fluidized again. Thus, the molded article is recovered to the original shape of the primary molded article having been memorized by the fixed phase.

As the lactic acid-based polymer to be used in this case, it is preferable to select one having a shape-recovery temperature of from 45 to 100° C. Namely, lactic acid-based polymers having Tg of from 45 to 100° C. are useful as biodegradable and absorbable implant materials to be embedded in vivo. The temperature range as specified above is determined for the following reason.

In general, plastic materials for medical use which should be sterilized are sterilized with ethylene oxide gas (EOG) in most cases except a few heat-resistant polymer materials, though sterilization with γ-ray is employed in some cases. Since the lower limit of EOG sterilization temperature is 40 to 45° C., it is necessary that these materials would not recover to the original shape at the sterilization temperature. It should be also avoided that the products are recovered to the original shape during storage. It is, therefore, necessary to select polymers having Tg of 45° C. or above which corresponds to the lower limit for the durability to high temperature in summer.

On the other hand, the upper limit of temperature should be specified, since a thermal treatment for the shape-recovery should be performed in vivo. To recover the molded article to the original shape, it may be directly heated with the use of a heating means such as laser, ultrasonic wave, high frequency wave or infrared radiation or a heat medium such as a hot air stream or hot water. However, it is necessary that vital tissues are never damaged thereby. Thus, the heating should be carried out at a temperature as low as possible. Contact with a heating medium at 100° C. is associated with little risk of burns, so long as the contact is completed within a short time, i.e., several seconds. Thus, this temperature may be referred to as the upper limit. To ensure improved safety, however, it is recommended to perform the shape-recovering treatment at a temperature of 45 to 70° C., preferably 50 to 65° C. By taking these factors into consideration, the shape-memory recovery temperature range is determined as from 45 to 100° C.

Among lactic acid-based polymers, highly suitable ones is poly-D,L-lactic acid as described above. This poly-D,L-lactic acid may be a copolymer obtained by mixing D-lactide with L-lactide at various ratios followed by ring-opening polymerization; a copolymer obtained by ring-opening polymerizing DL-lactide; a copolymer obtained by polymerizing a mixture of L-lactic acid with D-lactic acid; or a mixture of these copolymers.

Because of being a fundamentally amorphous glassy polymer, the poly-D,L-lactic acid shows elastic properties imparting a high deformability at the glass transition temperature or above. Thus, it can be deformed by enlargement, drawing, compression, twisting, etc. at a high ratio and yet recovered to the original shape at a ratio (shape recovery ratio) of almost 100%. The strength of this polymer can be regulated mainly by controlling the molecular weight and introducing somewhat crystalline phase thereinto. This polymer has an additional advantage that it can be hydrolyzed quickly in vivo, compared with crystalline poly-L-lactic acid, etc., owing to the amorphous properties.

Moreover, the glassy and amorphous poly-D, L-lactic acid may be mixed with a portion of biodegradable and absorbable polymers such as crystalline poly-L-lactic acid, poly-D-lactic acid, polyglycolic acid, amorphous polydioxanone, polycaprolactone or polytrimethylene carbonate. It is also preferable to use, either alone or as a mixture thereof, substantially amorphous shape-memory polymers obtained by copolymerizing lactides such as lactic acid/glycolic acid copolymer, lactic acid/dioxanone copolymer, lactic acid/caprolactone copolymer, lactic acid/ethylene glycol copolymer, lactic acid/propylene copolymer or lactide/ethylene oxide/propylene oxide copolymer (wherein lactic acid and lactide may be either L-, D-, DL- or D, L-isomers) with biodegradable and absorbable monomers.

The advantages achieved by using these crystalline homopolymer mixtures are, for example, as follows. Namely, various physical strengths as materials can be enhanced and the deforming and shape-memory temperatures can be elevated. Further, the degradation rate and the total absorption time in vivo can be regulated thereby. The advantages achieved by the intramolecular copolymerization of the poly-D, L-lactic acid with absorbable monomers are as follows. Namely, since the crystalline polymer can be converted into an amorphous one, various characteristic shape-memory/recovery functions can be imparted thereto. Furthermore, the degradation rate and the absorption rate can be thus controlled.

An additional technical basis for the present invention resides in the fact that these biodegradable and absorbable polymers can be subjected to the secondary molding at such a temperature as not deteriorating the polymer. These polymers are liable to be deteriorated, when molded by the conventional methods (injection molding, extrusion molding, compression molding, etc.) at Tm or above. For example, it is commonly observed that a polymer having a molecular weight of 400,000 is degraded into one having a molecular weight 1/10 times lower than the initial molecular weight. In contrast thereto, the polymers are scarcely deteriorated at Tf employed in the present invention. Thus, an extremely high shape recovery ratio can be established and materials with excellent shape-memory characteristics can be obtained.

The above-mentioned materials can be appropriately employed as various materials for treating vital tissues as will be describe d hereinafter (for example, those for vascular anastomosis, vascular ligation, tendon fixation, bone fixation, suture, preventing vascular reconstriction and preventing bone cement in marrow cavity from leakage and artificial hip joint) by first molding into the original shapes to be memorized (pipes, rings, yarns, plates, hemisphere cup shape and others) and then deforming to other shapes for easy handling. When allowed to stand in vivo, these materials are hydrolyzed with the passage of time and absorbed followed by discharge, since they are made of lactic acid-based polymers. That is to say, they would never remain in vivo as foreign matters. Because of being non-metallic, the lactic acid-based polymers would never cause halation in MRI or CT.

Although a shape-memory biodegradable and absorbable material made of a lactic acid-based polymer is deformed once in the above-mentioned case, the deformation may be performed repeatedly. Namely, a shape-memory biodegradable and absorbable material may be produced by deforming a molded article made of a lactic acid-based polymer and having a definite shape into another molded article having another shape at a temperature higher than the glass transition temperature thereof but lower than the crystallization temperature thereof (or 100° C. when the molded article has no crystallization temperature), then fixing said molded article to the thus deformed shape by cooling it as such to a temperature lower than the glass transition temperature, further deforming said molded article into another molded article having another shape at a temperature higher than the glass transition temperature but lower than said deformation temperature and fixing said molded article to the thus deformed shape by cooling it as such to a temperature lower than the glass transition temperature.

Such a shape-memory biodegradable and absorbable material is advantageous in that, when the temperature of the shape-memory biodegradable and absorbable material exceeds the second deformation temperature in the course of reheating, it can be recovered to the shape of the first-deformed molded article and, when the temperature thereof exceeds the first deformation temperature, it can be finally recovered to the shape of the original molded article. That is to say, shape-recovery at the intermediate step can be efficaciously utilized in shape-memory biodegradable and absorbable materials of this type.

In shape-memory biodegradable and absorbable materials of the present invention, mold articles are usually made of solid lactic acid-based polymers obtained by various molding procedures such as melt-molding, as the original molded article. It is also appropriate to employ foamed molded articles therefor. When a shape-memory biodegradable and absorbable material, which is prepared by deforming (for example, compression deforming) such a porous molded article into a substantially non-porous molded article having another shape at a temperature higher than the glass transition temperature (Tg) thereof but lower than the crystallization temperature (Tc) thereof (or 100° C. when the molded article has no crystallization temperature) and fixing this substantially non-porous molded article to the thus deformed shape by cooling it as such to a temperature lower than the glass transition temperature, is heated again to the above deformation temperature (Tf) or above, it can be recovered to the porous molded article of the original shape. When such a biodegradable and absorbable material is recovered to the original porous molded article and embedded in vivo, bodily fluids can quickly penetrate into the material via the open cells and thus the material is hydrolyzed. At the same time, tissue cells around the affected site can enter the material via the pores and proliferate therein. As a result, the material is replaced by the tissue cells and thus disappears within a relatively short period of time. Accordingly, such materials are highly useful as scaffolds, etc. for regenerating tissues.

As the original porous molded article, it is appropriate to use one having an expansion ratio of 2 to 3 and a porosity of about 50 to 70%. When a shape-memory material prepared from a porous molded article with an expansion ratio lower than 2 is embedded in vivo, bodily fluids and tissue cells cannot well enter the material. When a shape-memory material prepared from a porous molded article with an expansion ratio exceeding 3 is embedded in vivo, on the contrary, it is feared that the material can exert only an insufficient strength when embedded into an amputated part in a hard tissue (bone, etc.) in vivo. However, this wouldn't applicable to the case of soft tissues.

The shape-memory biodegradable and absorbable materials of the present invention can contain biologically active bioceramics powders or various drugs.

Examples of the bioceramics powders include powders of surface bioactive sintered hydroxyapatite, bioglass for living body use, crystallized glass for living body use, bioabsorbable neither calcined nor sintered hydroxyapatite, dicalcium phosphate, tricalcium phosphate, tetracalcium phosphate, octacalcium phosphate, calcite and diopsite. Either one of these bioceramics powders or a mixture thereof may be employed. When a shape-memory biodegradable and absorbable material containing such a bioceramics powder is embedded into bone tissue in vivo, the formation of the bone tissue on the surface of the material is induced by the bioceramics powder. Thus, the material can be fixed to the bone tissue within a short period of time followed by fixation or replacement. Namely, shape-memory biodegradable and absorbable materials of this type are highly useful as materials for bone fixation. In particular, bioceramics powder-containing shape-memory materials having been prepared by compression molding the above-mentioned porous molded articles are extremely efficacious in the reconstruction of bone tissue.

On the other hand, examples of the drugs used in the present invention include various remedies, antibacterial agents, bone growth factors, various hormones, physiologically active substances and various cytokines. When these drug-containing shape-memory biodegradable and absorbable materials are embedded in vivo, the drugs can be released at an almost constant rate. Thus, these materials can be appropriately employed as drug delivery system (DDS) bases. Among all, those containing growth factors such as the bone growth factors or cytokines as cited above are highly useful as materials for bone fixation or bone tissue reconstruction.

Next, particular embodiments of the shape-memory biodegradable and absorbable materials of the present invention will be described in greater detail by reference to the attached drawings.

FIG. 1 is a diagram which illustrates a shape-memory biodegradable and absorbable material for vascular anastomosis (hereinafter referred to simply as "shape-memory material for vascular anastomosis").

This shape-memory material for vascular anastomosis (1) is a cylindrical molded article made of a lactic acid-based polymer as described above. When heated to a definite temperature [i.e., the deformation temperature (Tf) as will be described hereinafter], it can be recovered to the memorized shape of small diameter pipes without applying any external force thereto.

Namely, this shape-memory material for vascular anastomosis (1) is prepared by enlarging and deforming a molded article (1a) made of a lactic acid-based polymer in the shape of small diameter pipes into another molded article in the shape of large diameter pipes at a temperature (Tf) higher than the glass transition temperature (Tg) thereof but lower than the crystallization temperature (Tc) thereof (or 100° C. when the molded article has no crystallization temperature) and then fixing said molded article to the shape of large diameter pipes by cooling it as such to a temperature lower than the glass transition temperature (Tg) to thereby make it to memorize the shape (small diameter pipes) of the original molded article (1a).

In the original molded article (1a) in the shape of small diameter pipes, the shape of the small diameter pipes is fixed by molding a lactic acid-based polymer to a temperature at which the material becomes moldable [i.e., higher than the melting temperature (Tm), if any, or the softening temperature (Ts)] and then solidifying it by cooling at ordinary temperature. Thus, both of the fixed and reversible phases have been solidified. The inner diameter of the small diameter pipes of this molded article (1a) should be smaller than the outer diameter of blood vessels. In usual, the inner diameter thereof is regulated depending on the size of the blood vessel to be anastomosed. From the viewpoint of strength, it is sufficient that this molded article has a thickness of from 0.5 to 3 mm.

This molded article (1a) may be enlarged and deformed by various methods. The most convenient method is one comprising enlarging the molded article (1a) by inserting therethrough an enlarging rod (101) with a sharp tip made of a metal or a synthetic resin while heating the molded article to the above-mentioned deformation temperature (Tf). Although the molded article (1a) can be enlarged about 15-fold (enlarging rate of inner diameter) at the maximum, an excessive enlargement might convert the lactic acid-based polymer into fibrils or make it less uniform while insufficient enlargement might result in only an unsatisfactory effect of shape-recovery. Thus, it is preferable to enlarge the molded article (1a) about 1.3- to 10-fold, still preferably about 1.5- to 6-fold.

To memorize the shape of small diameter pipes of the original molded article (1a), the enlargement and deformation should be carried out at a temperature (Tf) which is higher than the glass transition temperature (Tg) but lower than the crystallization temperature (Tc). Most of the lactic acid-based polymers to be used in the present invention have glass transition temperatures (Tgs) falling within a range of from 45 to 70° C. For the reasons as described above, the upper limit of the temperature (Tf) for the enlargement and deformation is 100° C. Usually, the molded article (1a) is enlarged and deformed at a relatively low temperature (about 50 to 70° C.).

As described above, the enlarging rod (101) is inserted through the molded article (1a) in the shape of the small diameter pipes while heating it to a temperature (Tf) higher than the glass transition temperature (Tg) but lower than the crystallization temperature (Tc). Thus, the reversible phase alone of the molded article (1a) is fundamentally molten and the polymer per se is softened to such an extent that it seems moldable. As a result, it can be enlarged into large diameter pipes. Next, the molded article is cooled at ordinary temperature lower than the glass transition temperature (Tg) as such (i.e., in the enlarged state) to thereby give a shape-memory material for vascular anastomosis (1) wherein the reversible phase has been solidified again and thus the shape of large diameter pipes is maintained by force. When the shape-memory material for vascular anastomosis (1) in the shape of large diameter pipes thus obtained is heated again to the above deformation temperature (Tf) or above, the reversible phase alone is molten. As a result, the molded article is recovered to the original molded article (1a) in the shape of small diameter pipes owing to the fixed phase. However, the shape-memory materials for vascular anastomosis of the present invention involve not only those wherein the fixed phase and the reversible phase independently form block phases but also those having no phase structure due to the interaction among molecules and exerting the same function.

This shape-memory material for vascular anastomosis (1) is finally sterilized with gas and stored. Since it is made of a lactic acid-based polymer having a glass transition temperature of from 45 to 70° C. as described above, there is no fear that the shape-memory material is recovered to the original shape at the gas sterilization temperature (40–45° C.) or during storage.

Figure 2:
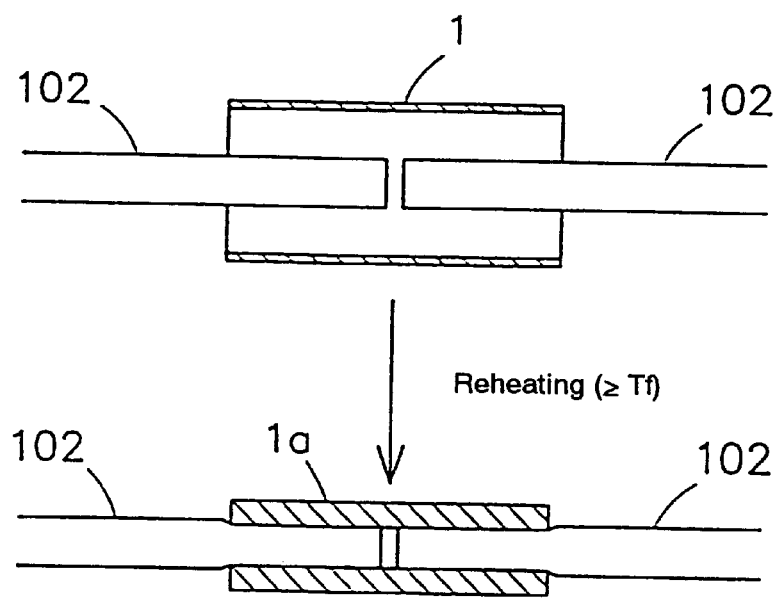
FIG. 2 is a diagram which illustrates how to use the above shape-memory material.

FIG. 2 is a diagram which illustrates how to use the above shape-memory material.

First, both ends of incised blood vessel sections (102, 102) are inserted from both openings of the shape-memory material for vascular anastomosis (1) in the shape of large diameter pipes. Next, the shape-memory material for vascular anastomosis (1) is heated again to the above deformation temperature (Tf) or above. The reheating can be conveniently performed by, for example, spraying a hot air stream or hot water (sterilized saline, etc.) heated to the above deformation temperature (Tf) or above, though other procedures such as laser heating, high frequency heating, ultrasonic wave heating, or IR heating can be used.

When thus heated again, the shape-memory material for vascular anastomosis (1) in the shape of large diameter pipes is quickly (within several seconds) recovered to the original molded article (1a) in the form of small diameter pipes and fixed while holding the ends of the blood vessel sections (102, 102). Thus, the blood vessel sections (102, 102) can be very easily anastomosed together. Compared with the conventional case wherein blood vessels are stitched together with a suture yarn, the anastomosis treatment can be very simply and easily performed, which can remarkably elevate the operation efficiency. Moreover, the reheating can be carried out at a relatively low temperature within a short period of time. Thus, this treatment is a highly safe one free from any fear of burns at the vessels or therearound.

In some cases, it is possible that, after recovering the shape-memory material for vascular anastomosis (1) to the original shape by reheating, the shape-memory material for vascular anastomosis (1) is somewhat flattened by using a fastener, etc. and then solidified by cooling. Thus, the shape-memory material for vascular anastomosis (1) can exhibit an improved force of holding and fixing the blood vessels. It is also possible that an adhesive (fibrin paste, etc.) is applied onto the inner face of the shape-memory material for vascular anastomosis (1) prior to the recovery and then the shape-memory material (1) is recovered to the original shape to thereby adhere the material (1) to the blood vessel sections (102) or adhere the blood vessel sections (102, 102) to each other.

When the blood vessel sections (102, 102) are anastomosed together by using the shape-memory material for vascular anastomosis (1) as described above, the blood vessels are bonded to each other through spontaneous healing. Subsequently, the shape-memory material for vascular anastomosis (1) comes in contact with bodily fluids and thus is hydrolyzed with the passage of time. Finally, it is absorbed in vivo and thus completely disappears. Although these phenomena proceed at different speeds depending on the type of the polymer, poly-D, L-lactic acid is appropriately employed therefor, since it can be considerably quickly degraded compared with poly-L-lactic acid.

In the shape-memory material for vascular anastomosis (1) according to embodiment, the original molding article (1a) in the shape of small diameter pipes is produced by melt-extrusion molding. However, other melt-molding procedures (injection molding, etc.) may be employed therefor. It is also possible to produce the molded article (1a) by applying or coating a solution of a lactic acid-based polymer in a volatile solvent onto the core material to form a thick cylindrical film around the core and, after solidification by drying, removing the core material. When the molded article (1a) is produced by applying or spraying as in the above case, drugs, etc. can be added to the polymer solution without any fear of denaturation. Accordingly, this method is particularly useful for producing a shape-memory material for vascular anastomosis (1) containing a drug, etc.

As the above-mentioned solvent, those in which lactic acid-based polymers are soluble are used. When a solution of a lactic acid-based polymer in a mixture of such a solvent with a non-solvent having a boiling point higher than that of the solvent per se is applied or sprayed onto the above core material and then dried, a foamed and porous molded article (1a) in the shape of small diameter pipes having an open cell structure can be obtained.

When a shape-memory material for vascular anastomosis (1) obtained by enlarging and deforming the foamed molded article (1a) thus obtained is recovered to the original foamed molded article (1a) by reheating and then embedded in vivo while holding the blood vessels, bodily fluids enter the shape-memory material (1) via the open cells. In this case, therefore, the contact area of the shape-memory material with the bodily fluids is considerably enlarged, compared with a shape-memory material having no open cell, and thus hydrolysis proceeds quickly. As a result, there is successfully achieved an advantage that the shape-memory material for vascular anastomosis (1) can be absorbed in vivo within about 1 to 3 months.

In this embodiment, the original molded article (1a) and the enlarged and deformed shape-memory material (1) are both in cylindrical shapes. However, the present invention is not restricted thereto and these molded articles can be molded into pipes having various sectional shapes, for example, ellipse, polygons including triangle and the like.

Figure 3:
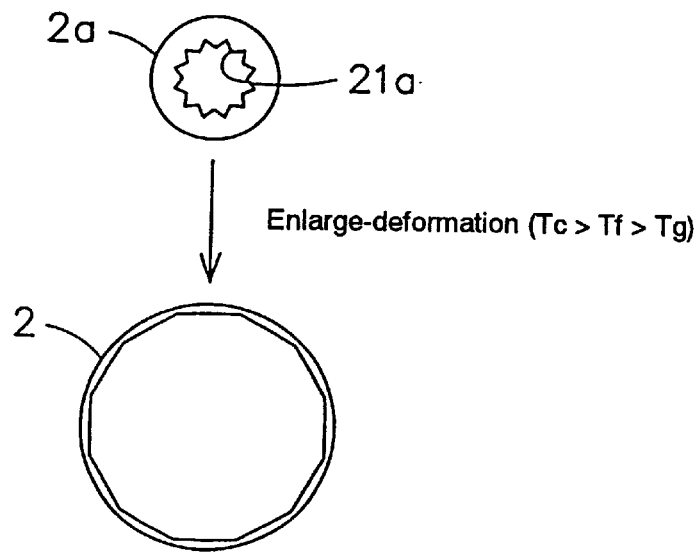
FIG. 3 is a diagram which illustrates a shape-memory material for vascular anastomosis according to another embodiment of the present invention.

FIG. 3 is a diagram which illustrates a shape-memory material for vascular anastomosis according to another embodiment of the present invention.

In this shape-memory material for vascular anastomosis (22), a molded article (2a) made of a lactic acid-based polymer and having a shape of small diameter pipes has a crimpy inner face (21a). This molded article (2a) is enlarged and deformed into large diameter pipes by heating it to a temperature (Tf) higher than the glass transition temperature (Tg) but lower than the crystallization temperature (Tc) thereof (or 100° C. when the molded article has no crystallization temperature). Then it is fixed to this shape by cooling it as such to a temperature lower than the glass transition temperature (Tg).

When blood vessels are anastomosed with the use of this shape-memory material for vascular anastomosis (2) by reheating it in the same manner as the one described above, the blood vessels can be tightly held and fixed all around owing to the crimpy inner face (21a) of the original molded article (2a) in the shape of small diameter pipes. As a result, it is ensured that the blood vessels would never fall off from the shape-memory material for vascular anastomosis (2).

The inner face of the molded article (2a) may be crimped not only lengthwise. Namely, it may be draped vertically so that the ends of the incised blood vessels can be brought close and adhered to each other easily.

Figure 4:
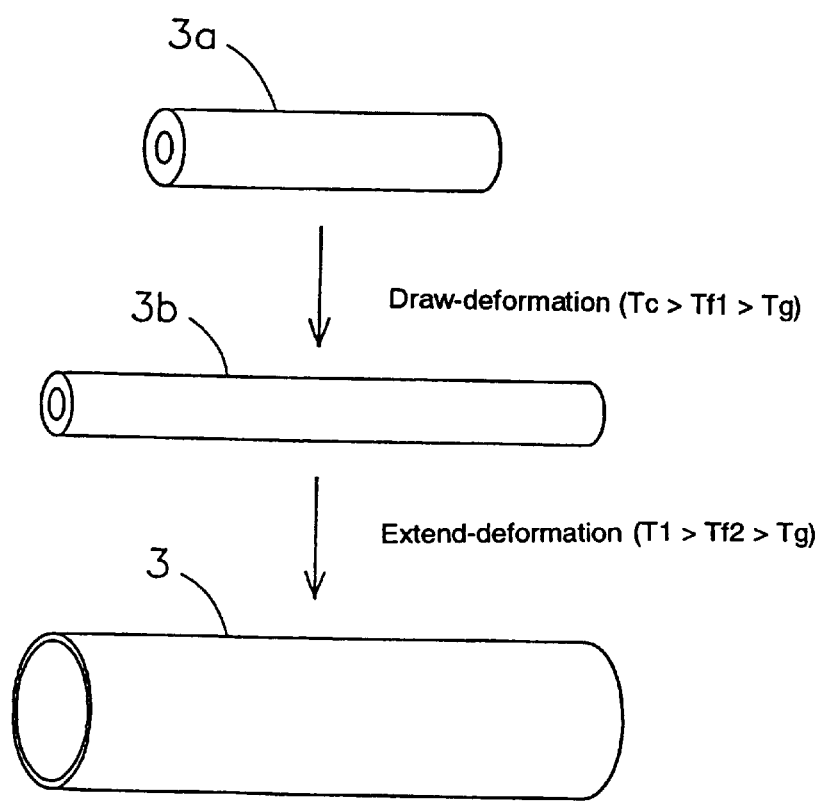
FIG. 4 is a diagram which illustrates a shape-memory material for vascular anastomosis according to another embodiment of the present invention.
Figure 5:
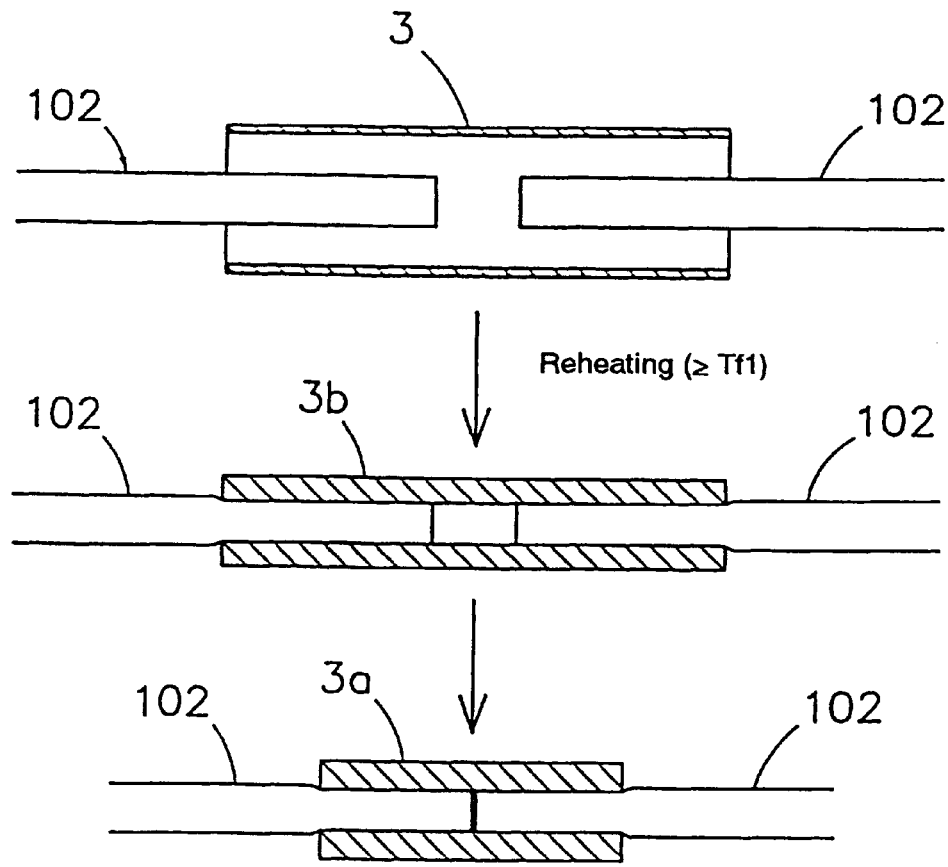
FIG. 5 is a diagram which illustrates how to use the above shape-memory material.

FIG. 4 is a diagram which illustrates a shape-memory material for vascular anastomosis according to another embodiment of the present invention, while FIG. 5 is a diagram which illustrates how to use the above shape-memory material.

This shape-memory material for vascular anastomosis (3) is prepared by drawing and deforming a molded article (3a) made of a lactic acid-based polymer and having a shape of small diameter pipes into another molded article (3b) having another shape of longer small diameter pipes at a temperature (Tf1) higher than the glass transition temperature (Tg) thereof but lower than the crystallization temperature (Tc) thereof (or 100° C. when the molded article has no crystallization temperature), then fixing said molded article to the thus deformed shape by cooling it as such to a temperature lower than the glass transition temperature, further extending this molded article (3b) into another molded article having another shape of large diameter pipes at a temperature (Tf2) higher than the glass transition temperature (Tg) but lower than the above deformation temperature (Tf1) and fixing said molded article to the thus extended shape by cooling it as such to a temperature lower than the glass transition temperature.

When the temperature of the shape-memory material for vascular anastomosis (3) exceeds the second deformation temperature (Tf2) in the course of reheating to the first deformation temperature (Tf1) or above, it can be recovered to the shape of the first-deformed molded article (3b) of longer and small diameter pipes. When heating is further continued and the temperature thereof exceeds the first deformation temperature (Tf1), it can be finally recovered to the shape of the original molded article (3a), i.e., small diameter pipes.

As FIG. 5 shows, both ends of incised blood vessel sections (102, 102) are inserted from both openings of the shape-memory material for vascular anastomosis (3). Next, the shape-memory material for vascular anastomosis (3) is heated again and recovered to the molded article (3b) in the shape of longer and small diameter pipes. Thus the blood vessel sections (102, 102) are tightly held and fixed by the molded article (3b). Subsequently, the molded article (3b) further constricts lengthwise to the original shape of the molded article (3a) while holding and fixing the blood vessel sections (102, 102). Thus, the blood vessel sections (102, 102) can be brought close together and anastomosed.

It is desirable that the second deformation temperature (Tf2) is lower by at least 10° C. than the first deformation temperature (Tf1). When the difference between these temperatures is less than 10° C., the shape-memory material for vascular anastomosis (3) is recovered almost simultaneously to the molded article (3b) and the molded article (3a) in the course of reheating. As a result, the blood vessel sections (102, 102) can be hardly brought close together and anastomosed. When the difference between these temperatures is more than 10° C., on the other hand, the recovery of the shape of the shape-memory material for vascular anastomosis (3) to the molded article (3b) can be completed during the reheating proceeds from the second deformation temperature (Tf12) to the first deformation temperature (Tf1). Thus, the recovery of the molded articles (3b) and (3a) can proceed stepwise and the blood vessel sections (102, 102) can be brought close together and anastomosed. It is preferable that the difference between the first deformation temperature (Tf1) and the second deformation temperature (Tf2) is from 20 to 30° C. Examples of materials appropriately satisfying this requirement include lactic acid-based polymers having a partly crystallized phase or containing a portion of a crystalline lactic acid-based polymer.

It is also preferable in this shape-memory material for vascular anastomosis (3) to use a molded article having a crimpy inner face as the original molded article (3a) in the shape of small diameter pipes so that, after the shape-recovery by reheating, blood vessels can be tightly held and fixed owing to the crimpy inner face thereof.

Figure 6:
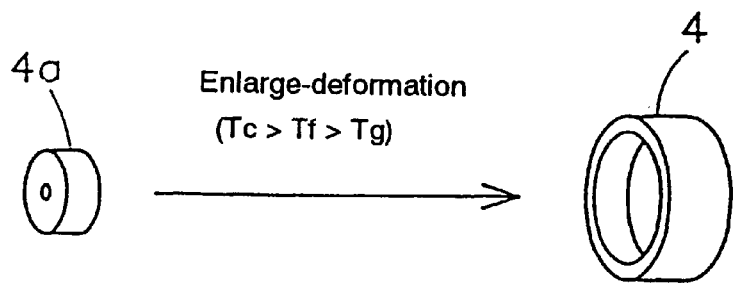
FIG. 6 is a diagram which illustrates a shape-memory material for vascular ligation according to another embodiment of the present invention.
Figure 7:
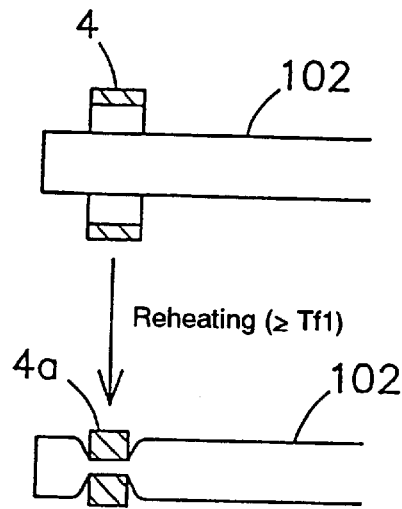
FIG. 7 is a diagram which illustrates how to use the above shape-memory material.

FIG. 6 is a diagram which illustrates a shape-memory biodegradable and absorbable material for vascular ligation (hereinafter referred to simply as "shape-memory material for vascular ligation") according to another embodiment of the present invention, while FIG. 7 is a diagram which illustrates how to use the above shape-memory material.

This shape-memory material for vascular ligation (4) is made of a molded article of a lactic acid-based polymer in the shape of rings. When it is heated to a deformation temperature [i.e., the deformation temperature (Tf) as will be described hereinafter], it can be recovered to the memorized shape of small diameter pipes without applying any external force thereto.

That is to say, this shape-memory material for vascular ligation (4) is prepared by enlarging and deforming a molded article (4a) made of a lactic acid-based polymer in the shape of small diameter rings into another molded article in the shape of large diameter rings at a temperature (Tf) higher than the glass transition temperature (Tg) thereof but lower than the crystallization temperature (Tc) thereof (or 100° C. when the molded article has no crystallization temperature) and then fixing said molded article to the shape of large diameter rings by cooling it as such to a temperature lower than the glass transition temperature (Tg).

When heated to the deformation temperature (Tf) or above, this shape-memory material for vascular ligation (4) in the shape of large diameter rings can be quickly recovered to the original molded article (4a) in the shape of small diameter rings. As FIG. 7 shows, this shape-memory material for vascular ligation (4) is put into the end of a blood vessel (102) to be ligated. Then it is reheated by bringing into contact with a hot air stream or hot water (sterilized physiological saline) at deformation temperature (Tf) or above. As a result, it is immediately recovered to the original molded article (4a) in the shape of small diameter rings and thus the end of the blood vessel (102) can be tightly ligated all around thereby, thus achieving stanching. In this case, it is possible that the shape-memory material is somewhat flattened by using a fastener, etc. and then solidified by cooling. Thus, the safety can be improved since the end of the blood vessel (102) is ligated more strongly. If necessary, hemostatic drugs, etc. may be applied to the ligated part of the blood vessel (102).

The inner diameter of the original molded article (4a) in the shape of small rings should be regulated so as to ensure sufficient ligation of the blood vessel (102). More particularly speaking, it is preferable, by taking into consideration the size of the blood vessel to be ligated, that the molded article (4a) is in the shape of rings having an inner diameter of from about 0.1 to 1.5 mm. In this case, the blood vessel (102) can be ligated more strongly by crimping the inner face of the molded article (4a). It is sufficient that the width of this molded article (4a) ranges from about 0.3 to 5 mm.

It is preferable that the original molded article (4a) is enlarged and deformed into a shape-memory material for vascular ligation (4) in the shape of large diameter ring, i.e., having an inner diameter enlarged 3- to 10-fold, by a convenient procedure, for example, insertion of an enlarging rod (101) through the molded article (4a) as described above. When the shape-memory material (4) is enlarged less than 3-fold, it cannot be well put into the blood vessel. When the shape-memory material (4) is excessively enlarged (i.e., more than 10-fold), it is feared that the shape-memory material (4) might suffer from deterioration in the strength due to heterogenization. Thus, both of these cases are undesirable.

In this embodiment, the original molded article (4a) and the enlarged and deformed shape-memory material (4) are both in the shape of round rings. However, it is needless to say that these rings maybe out of round (for example, ellipse, polygons including triangle and the like).

Figure 8:
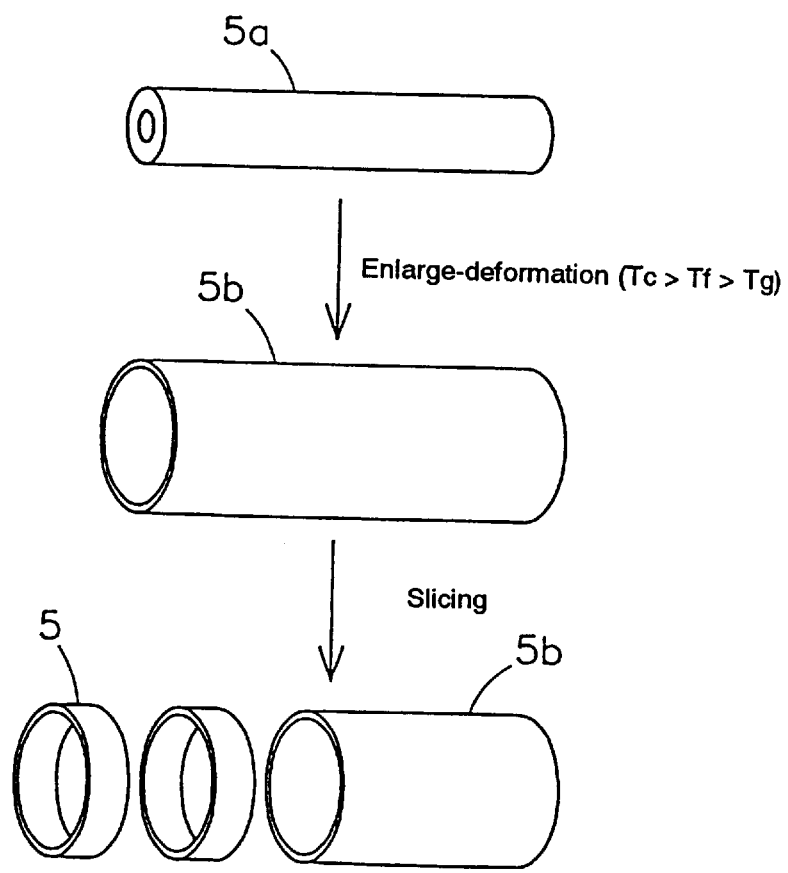
FIG. 8 is a diagram which illustrates a shape-memory material for vascular ligation according to another embodiment of the present invention.

FIG. 8 is a diagram which illustrates a shape-memory material for vascular ligation according to another embodiment of the present invention.

This shape-memory material for vascular ligation (5) is prepared by enlarging and deforming a molded article (5a) made of a lactic acid-based polymer in the shape of small diameter pipes into another molded article (5b) in the shape of large diameter pipes at a temperature (Tf) higher than the glass transition temperature (Tg) thereof but lower than the crystallization temperature (Tc) thereof (or 100° C. when the molded article has no crystallization temperature) and then fixing said molded article (5b) to the shape of large diameter pipes by cooling it as such to a temperature lower than the glass transition temperature followed by cutting into round slices to give large diameter rings.

When heated to the deformation temperature (Tf) or above, the shape-memory material for vascular ligation (5) in the shape of large diameter rings can be recovered to the shape of small diameter rings obtained by cutting the original molded article (5a) in the shape of small diameter pipes into round slices. This shape-memory material for vascular ligation (5) in the shape of a large diameter ring is put into the end of a blood vessel and reheated by bringing into contact with a hot air stream or hot water (sterilized physiological saline) at deformation temperature (Tf) or above. As a result, it is immediately recovered to the original shape of a small diameter ring and thus the end of the blood vessel can be tightly ligated, thus achieving stanching.

The inner diameter of the original molded article (5a) in the shape of small diameter pipes should be regulated to about 0.1 to 1.5 mm by taking the size of the blood vessel to be ligated into consideration. It is desirable that the molded article (5a) has a crimpy inner face so as to improve its ligating performance. Similar to the above-mentioned case, it is preferable that the original molded article (5a) is enlarged and deformed into amolded article (Sb) in the form of large diameter pipes so that the inner diameter is enlarged 3- to 10-fold. It is sufficient that the width of the shape-memory material (5) in the shape of large diameter rings ranges from about 0.3 to 5 mm.

Figure 9:
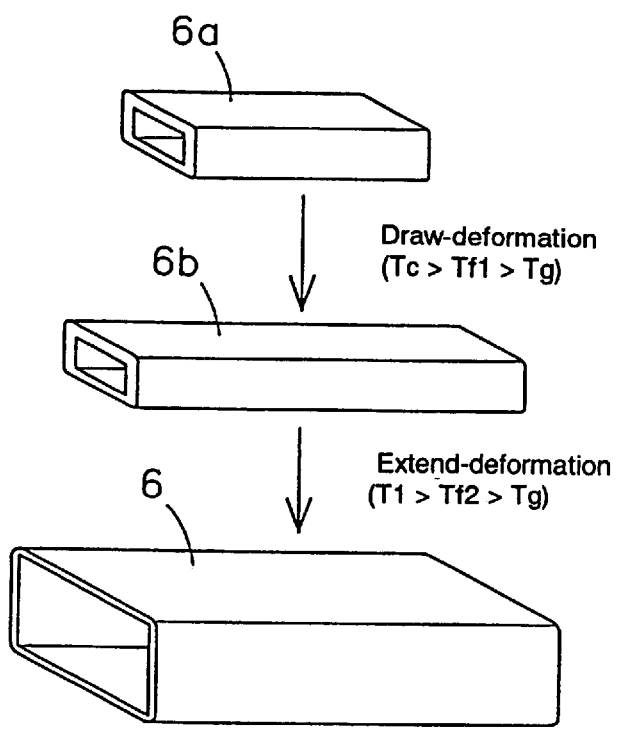
FIG. 9 is a diagram which illustrates a shape-memory material for tendon fixation according to another embodiment of the present invention.
Figure 10:
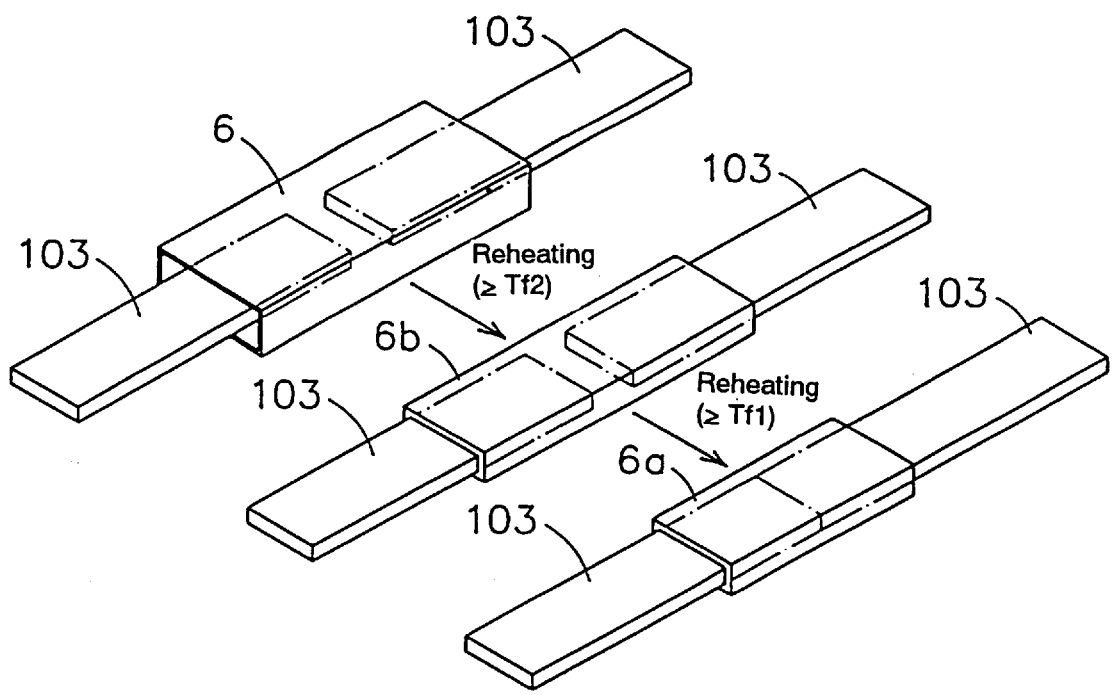
FIG. 10 is a diagram which illustrates how to use the above shape-memory material.

FIG. 9 is a diagram which illustrates a shape-memory biodegradable and absorbable material for tendon fixation (hereinafter referred to as "shape-memory material for tendon fixation") according to another embodiment of the present invention, while FIG. 10 is a diagram which illustrates how to use it.

This shape-memory material for tendon fixation (6) is prepared by drawing and deforming a molded article (6a) made of a lactic acid-based polymer in the shape of almost square small pipes having a flat opening area into another molded article (6b) in the shape of longer pipes having a small opening area at a temperature higher than the glass transition temperature (Tg) thereof but lower than the crystallization temperature (Tc) thereof (or 100° C. when the molded article has no crystallization temperature), then fixing said molded article (6b) to the shape by cooling it as such to a temperature lower than the glass transition temperature (Tg), next extending and deforming the molded article (6b) into another molded article in the shape of almost square pipes with a larger opening at a temperature (Tf2) higher than the glass transition temperature (Tg) but lower than the former deformation temperature (Tf1), and then fixing said molded article to the shape by cooling it as such to a temperature lower than the glass transition temperature (Tg).

When the temperature of the shape-memory material for tendon fixation (6) exceeds the second deformation temperature (Tf2) in the course of reheating to the first deformation temperature (Tf1) or above, it can be recovered to the shape of the intermediate molded article (6b) of longer small diameter pipes. When heating is further continued and the temperature thereof exceeds the first deformation temperature (Tf1), it can be finally recovered to the shape of the original molded article (6a).

As FIG. 10 shows, both ends of incised belt-like tendon sections (103, 103) are inserted from both openings of the shape-memory material for tendon fixation (6). Next, the shape-memory material for tendon fixation (6) is heated again. Thus, the shape-memory material (6) is constricted both lengthwise and breadthwise and thus recovered to the molded article (6b) in the shape of a long, flat and almost square pipe having a small opening areas and, therefore, the tendon sections (103, 103) are tightly held and fixed thereby. Subsequently, it is constricted lengthwise while tightly holding the tendon sections (103, 103) and recovered to the original molded article (6a) in the shape of a short, flat and almost square pipe having a small opening area. Thus, the tendon sections (103, 103) can be brought close together and fixed.

To ensure the tight holding and fixation of the belt-like tendon sections (103), it is necessary that the original molded article (6a) is in the form of a flat and almost square pipe having a smaller size (length and width) than that of the tendon (103). More particularly speaking, it is preferable that the molded article (6a) is in the shape of a flat and almost square pipe of 2 to 10 mm in inner length, 7 to 30 mm in inner width and 0.1 to 3 mm in thickness. It is also preferable that this molded article (6a) has a crimpy inner face so as to improve the performance of holding and fixing the tendons.

It is preferable that the first draw-deformation is carried out so that the molded article (6a) is lengthened 1.5- to 10-fold, preferably about 2- to 6-fold. Similarly, it is preferable that the second extend-deformation is carried out so that the molded article (6b) is extended about 3- to 10-fold, in length and width. Similar to the above-mentioned case of the shape-memory material for vascular anastomosis (3), the difference between the first deformation temperature (Tf1) and the second adeformation temperature (Tf2) should be at least 10° C., preferably 20 to 30° C.

The shape-memory material for tendon fixation (6) according to this embodiment is subjected to deformation twice, as described above. It is also possible that the original molded article (6a) in the shape of flat and almost square pipes with a small opening area is enlarged and deformed lengthwise and breadthwise once by heating to a temperature (Tf) higher than the glass transition temperature (Tg) thereof but lower than the crystallization temperature (Tc) thereof (or 100° C. when the molded article has no crystallization temperature) and then cooled to give a shape-memory material in the shape of almost square pipes having an opening area larger than that of the original molded article (6a). When reheated to the glass transition temperature or above, this shape-memory material for tendon fixation , which has been merely enlarged and deformed, can be constricted lengthwise and breadthwise and thus recovered to the original shape-memory biodegradable and absorbable material (6a) in the shape of flat and almost square pipes. In this case, incised tendons can be tightly held and fixed thereby too.

Figure 11:
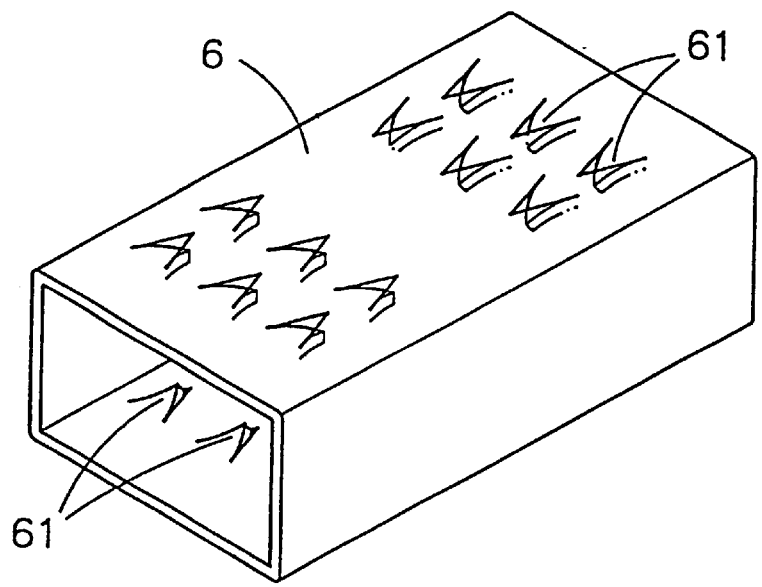
FIG. 11 is a diagram which illustrates a shape-memory material for tendon fixation according to another embodiment of the present invention.

FIG. 11 is a diagram which illustrates a shape-memory material for tendon fixation according to another embodiment of the present invention.

In this shape-memory material for tendon fixation, a number of V-shaped cut and lifted portions (61) toward the inner side are formed on the top and bottom faces of the above-mentioned shape-memory material for tendon fixation (6) in the shape of an almost square pipe having a large opening area. These cut and lifted portions (61) are heated to the glass transition temperature (Tg) or above and the cut and lifted portions are constricted and recovered followed by solidification by cooling.

When this shape-memory material for tendon fixation (6) is recovered to the original shape by reheating so as to fix tendons, the cut and lifted portion (61), which have been preliminarily constricted and solidified, strike through the top and bottom faces, thus achieving an advantage of surely preventing the tendons from falling off after the completion of the fixation.

As FIG. 11 shows, it is preferable that the tip of each of the V-shaped cut and lifted portion (61) is located toward the center of the shape-memory material (6), since the cut and lifted portions can well strike through tendons and thus achieve an improved effect of preventing the tendons from falling off.

Further illustration on the constitution of this shape-memory material for tendon fixation is omitted, since it is the same as that of the shape-memory material for tendon fixation (6) as described above.

Figure 12:
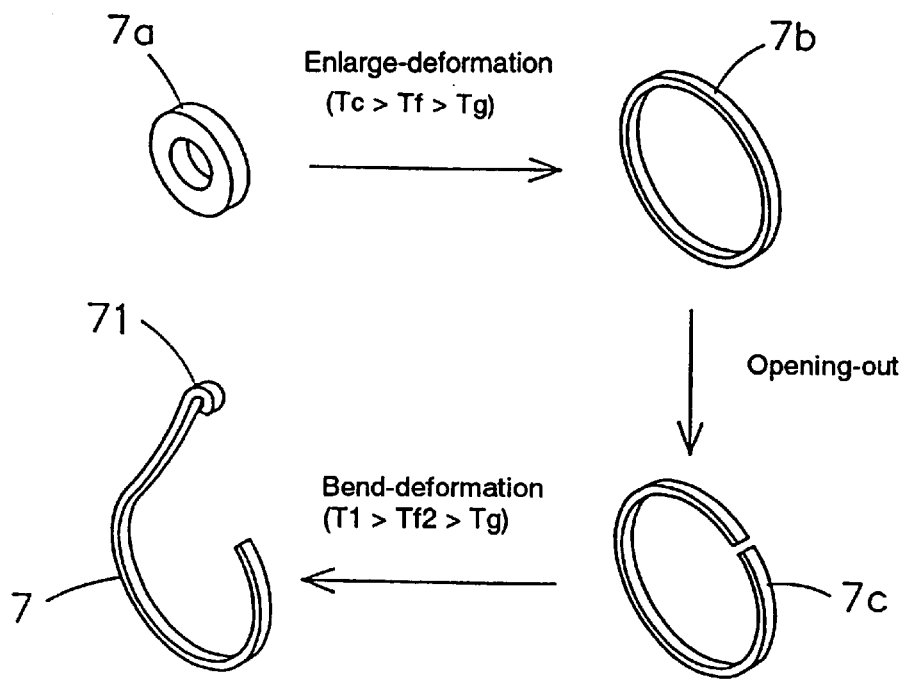
FIG. 12 is a diagram which illustrates a shape-memory material for suture according to another embodiment of the present invention.
Figure 13:
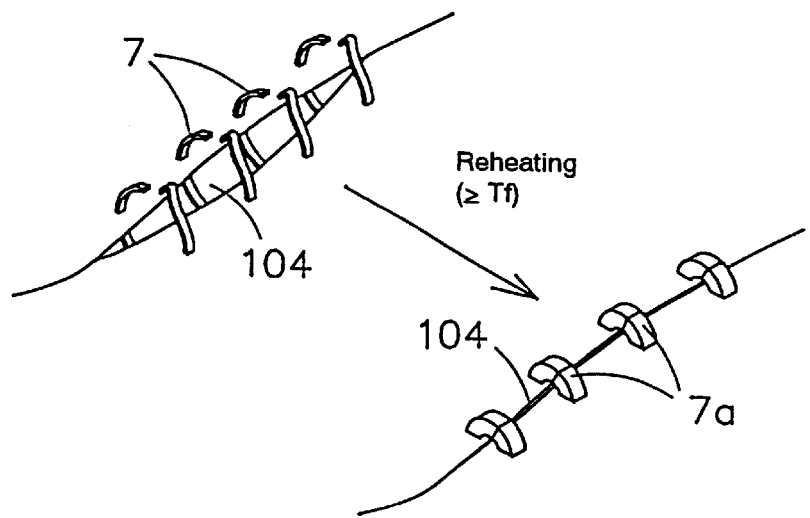
FIG. 13 is a diagram which illustrates how to use the above shape-memory material.

FIG. 12 is a diagram which illustrates a shape-memory biodegradable and absorbable material for suture (hereinafter referred to as "shape-memory material for suture") according to another embodiment of the present invention, while FIG. 13 is a diagram which illustrates how to use the same.

This shape-memory material (7) for suture is made of a molded article of a lactic acid-based polymer in the shape of opened-out rings. When it is heated to a deformation temperature [i.e., the deformation temperature (Tf) as will be described hereinafter], it can be recovered to the memorized shape of opened-out small diameter rings without applying any external force thereto.

Namely, this shape-memory material for suture (7) is prepared by enlarging and deforming a molded article (7a) made of a lactic acid-based polymer in the shape of small diameter rings into another molded article (7b) in the shape of large diameter rings at a temperature higher than the glass transition temperature (Tg) thereof but lower than the crystallization temperature (Tc) thereof (or 100° C. when the molded article has no crystallization temperature), opening-out said molded article (7b) in the shape of large diameter rings, bending a part of the thus opened-out molded article (7c) so as to match with a suture needle to give a hook (71), and then fixing it to this shape by cooling it as such to a temperature lower than the glass transition temperature (Tg).

When heated again to the definite temperature (Tf) or above, the shape-memory material for suture (7) can be recovered to the former molded article (7a) in the shape of small diameter rings having been opened-out. As FIG. 13 shows, the hook (71) of this shape-memory material for suture (7) is provided with a suture needle with which an incised site (104) of a living body is sewed in the desired stitches. Thus the incised site (104) is tentatively sewed up by passing the shape-memory material (7) through both ends thereof. Subsequently, the shape-memory material (7) is reheated to the deformation temperature (Tf) or above with a heat source (hot water, hot air stream, etc.). Then the shape-memory material (7) is quickly recovered to the original molded article (7a) in the shape of opened-out small diameter rings. Thus, the incised site (104) can be conveniently sewed up without fail.

To tightly sew up the incised site (104), it is preferable that the original molded article (7a) in the shape of small diameter rings has an inner diameter of from about 0.1 to 5 mm, an outer diameter of from about 0.3 to 7 mm and a length of from about 0.3 to 5 mm. It is also preferable that the molded article (7a) is enlarged and deformed so that the molded article (7b) in the shape of large diameter rings has an inner diameter 3 to 7 times larger than that of the molded article (7a). In this embodiment, the original molded article (7a) and the enlarged and deformed one (7b) are both in the shape of round rings. However, it is needless to say that these rings may be out of round (for example, ellipse, polygons including triangle and the like). It is desirable that original molded article (7a) is in the shape of opened-out small diameter rings wherein both ends of the opened-out part overlap each other. This is because the incised site (104) can be sewed up more tightly after the molded article is recovered to the original shape by reheating.

In this embodiment, an end of the molded article (7c) in the shape of opened-out large diameter rings is bent to form the hook (71). Alternatively, the molded article (7a) in the shape of small diameter rings may be enlarged and deformed into the molded article (7b) in the shape of large diameter rings at the above-mentioned deformation temperature (Tf) followed by cooling it as such to a temperature lower than the glass transition temperature (Tg) to thereby fix the shape. Then it is opened-out as done in the case of the molded article (7c) to give a shape-memory material for suture.

Figure 14:
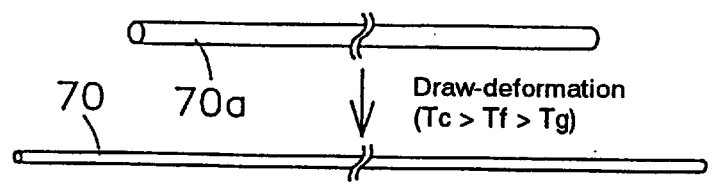
FIG. 14 is a diagram which illustrates a shape-memory material for suture according to another embodiment of the present invention.

FIG. 14 is a diagram which illustrates a shape-memory material for suture according to another embodiment of the present invention. This shape-memory material for suture (70) is made of a lactic acid-based polymer in the shape of yarns. When it is heated to a deformation temperature [i.e., the deformation temperature (Tf) as will be described hereinafter], it can be shortened to the memorized shape of thick yarns without applying any external force thereto.

This shape-memory material for suture (70) is prepared by processing a lactic acid-basedpolymer into amolded article (70a) in the shape of thick yarns by, for example, melt-extrusion molding, drawing and deforming the molded article (70a) into another molded article in the shape of yarns longer and thinner than the above ones at a temperature higher than the glass transition temperature (Tg) thereof but lower than the crystallization temperature (Tc) thereof (or 100° C. when the molded article has no crystallization temperature) and then fixing said molded article to the shape of thin yarns by cooling it as such to a temperature lower than the glass transition temperature (Tg).

This shape-memory material for suture (70) in the shape of yarns is used in sewing incised sites in vivo similar to the conventional suture yarns. However, it is unnecessary to closely tie up these yarns, as done in the existing cases. That is to say, an incised site is loosely sewed up with such a yarn of the shape-memory material (70) tentatively. Next, the shape-memory material (70) is reheated by bringing into contact with hot air stream or hot water (sterilized physiological saline) at the glass transition temperature (Tg) or above. Thus, the shape-memory material (70) is immediately recovered to the original shape of thick yarn and thus the incised site can be fastened, thus considerably relieving the labor for sewing.

It is appropriate that the original molded article (70a) in the shape of yarns has a diameter of about 0.2 to 1 mm, since yarns of such size have a sufficient tensile strength and suffer from no trouble of cutting. It is also preferable that the molded article (70a) is drawn and deformed 1.5- to 10-fold, still preferably 2- to 6-fold.

In this embodiment, the original molded article (70a) and the shape-memory material (70) for suture are both in the shape of yarns with round section. However, these yarns may have oval or rectangular sections. To obtain a shape-memory material for suture in the shape of yarns with rectangular section, it is appropriate that the original molded article with rectangular section has a thickness of from 0.2 to 0.4 mm and a width of from about 0.5 to 1.5 mm.

Figure 15:
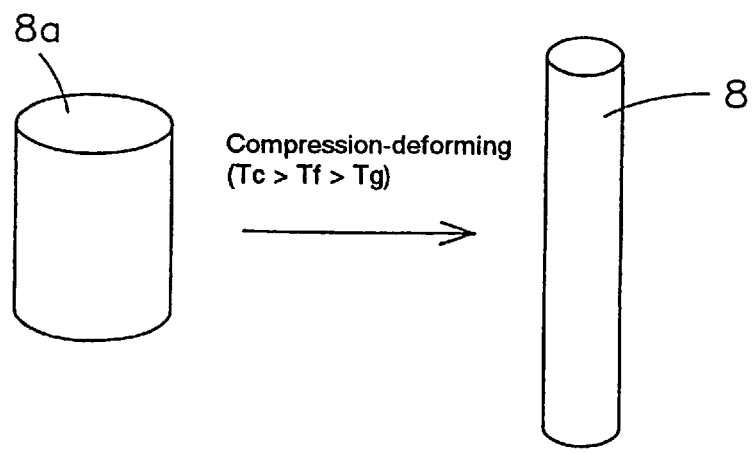
FIG. 15 is a diagram which illustrates a shape-memory material for bone fixation according to another embodiment of the present invention.
Figure 16:
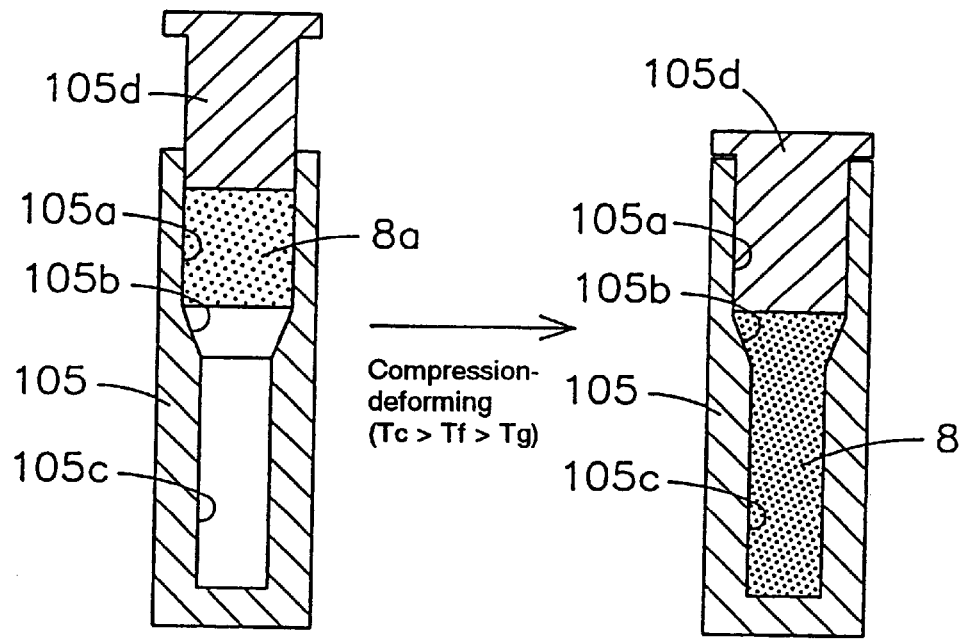
FIG. 16 is a diagram which illustrates the compression deforming of the above shape-memory material.
Figure 17:
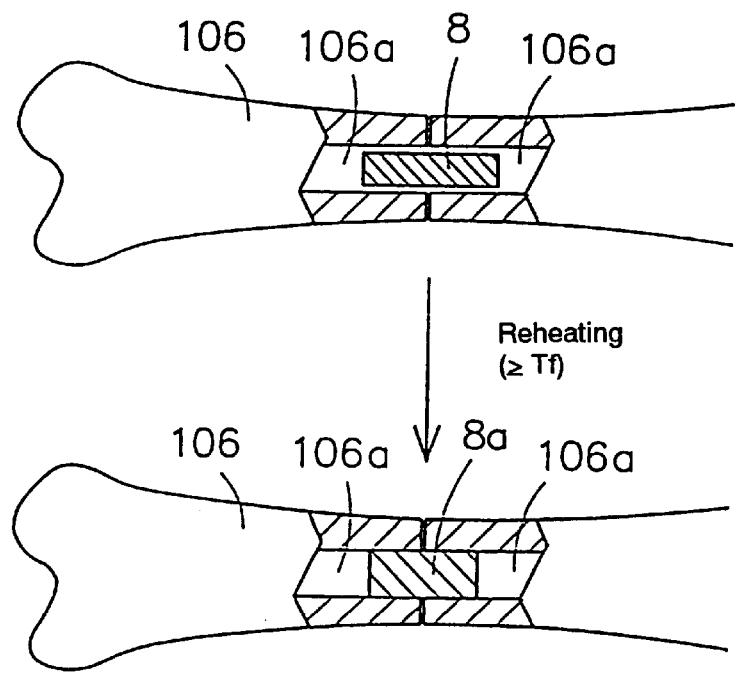
FIG. 17 is a diagram which illustrates how to use the above shape-memory material.

FIG. 15 is a diagram which illustrates a shape-memory biodegradable and absorbable material for bone fixation and union (hereinafter referred to simply as "shape-memory material for bone fixation") according to another embodiment of the present invention, while FIG. 16 is a diagram which illustrates the compression deforming of the above shape-memory material and FIG. 17 is a diagram which illustrates how to use the above shape-memory material.

This shape-memory material for bone fixation (8) is a molded article made of a lactic acid-based polymer in the shape of bars. When it is heated to a deformation temperature [i.e., the deformation temperature (Tf) as will be described hereinafter], it can be recovered to the memorized shape of thick and short bars, compared with those before reheating, without applying any external force thereto.

This shape-memorymaterial forbone fixation (8) is prepared by compressing and deforming amolded article (8a) made of a lactic acid-based polymer in the shape of thick and round bars into another molded article in the shape of round bars longer and thinner than said ones at a deformation temperature higher than the glass transition temperature (Tg) thereof but lower than the crystallization temperature (Tc) thereof (or 100° C. when the molded article has no crystallization temperature) and then fixing said molded article to the shape of thin and round bars by cooling it as such to a temperature lower than the glass transition temperature (Tg).

When this shape-memory material for bone fixation (8) is heated to the deformation temperature (Tf) or above, it is immediately recovered to the original molded article (8a) in the shape of thick and round bars. As FIG. 17 shows, therefore, this shape-memory material for bone fixation (8) is used as a substitute for conventional intermedually nails. Namely, the shape-memory material (8) is inserted equally into the marrow cavities (106a, 106a) of both sections (106, 106) of a broken or incised bone. Then this shape-memory material is reheated by, for example, bringing into contact with hot water (sterilized saline) at the deformation temperature (Tf) or above. As a result, the shape-memory material for bone fixation (8) is recovered to the original molded article (8a) in the shape of a thick and round bar and comes in contact closely to the inner faces of the marrow cavities (106a, 106a). Namely, the shape-memory material (8) is fixed tightly and cannot fall off. Thus, the bone sections (106, 106) can be easily and surely fixed together.

It is also possible to use this shape-memory material for bone fixation (8) as a substitute for conventional bone fixation pins. In this case, holes having a diameter somewhat larger than the shape-memory material for bone fixation (8) are formed in the bone section to be fixed. Then the shape-memory material (8) is inserted into the holes and reheated in the same manner as the one described above. Thus, the shape-memory material is recovered to the original shape so as to fix the bone section.

The original molded article (8a) in the shape of thick and round bars may be formed by various molding methods, for example, melt molding, injection molding or press molding. It may be as large as the conventional intermedually nails or bone fixation pins.

For the compression deforming of the original molded article (8a), for example, the procedure shown in FIG. 16 may be appropriately used. In this compression deforming procedure, a mold (105) is used in which coaxially provided with a large diameter cylindrical holding cavity (105a) having a large cross-sectional opening area and a small diameter cylindrical, bottomed molding cavity (105c) having a small cross-sectional opening area and a contraction part (105b) having an inner face tapered toward the bottom which is located between the two cylindrical cavities (105a, 105c). The molded article (8a) is introduced into the holding cavity (105a). Next, the molded article (8a) is continuously or intermittently pressing into the molding cavity (105c) by a pressing male die (105d) at the deformation temperature (Tf) as described above and then fixed to the shape by cooling as such to thereby give a shape-memory material (8) in the shape of thin and round bars.

In this procedure, it is preferable that the opening area ratio of the holding cavity (105a) to the molding cavity (105c) is controlled within a range of from 1.5 to 6.0 so as to regulate the deformation ratio [i.e., sectional area of molded article (8a)/sectional area of shape-memory material (8)] substantially from 1.5 to 6.0. When the deformation ratio is less than 1.5, the resultant shape-memory material has only an insufficient effect of shape-recovery. When the deformation ratio exceeds 6.0, on the other hand, there arises another problem that the material becomes porous or fibrous, i.e., heterogenization.

It is highly useful to add to this shape-memory material for bone fixation (8) from 10 to 60% by weight, preferably 20 to 50% by weight, of a biologically active bioceramics powder. When the bioceramics powder-containing shape-memory material for bone fixation (8) thus obtained is inserted into a marrow cavity or a hole formed by drilling as described above, it is well closed to the surrounding tissues due to the shape-recovery. As a result, the bioceramics powder exposed on the surface of the shape-memory material (8) or exposed therefrom due to hydrolysis contributes to the formation of the bone tissues on the surface of the shape-memory material (8) at a high reproducibility. Thus, the shape-memory material (8) can be attached and fixed to the bone within a short period of time.

As the bioceramics powder, the above-mentioned ones may be used. Among all, neither calcined nor sintered hydroxyapatite and tricalcium phosphate are highly useful therefor, since these bioceramics powders show excellent capability of inducing and forming bone tissues and have been employed in practice frequently.

In this embodiment, the original molded article (8a) and the shape-memory material for bone fixation (8) are both in the shape of round bars. When employed as, for example, a substitute of intermedually nails, however, these materials may be in the shape of square bars or appropriately curved ones. That is, they may have any sectional shape or curved form, so long as they are hollow and long bars.

Figure 18:
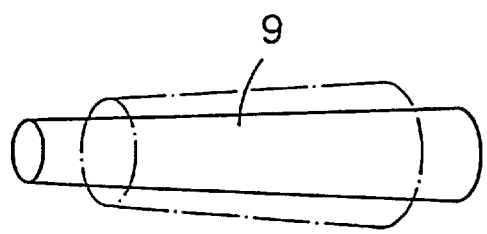
FIG. 18 is a diagram which illustrates a shape-memory material for fixing a bone plate for fracture fixation according to another embodiment of the present invention.
Figure 19:
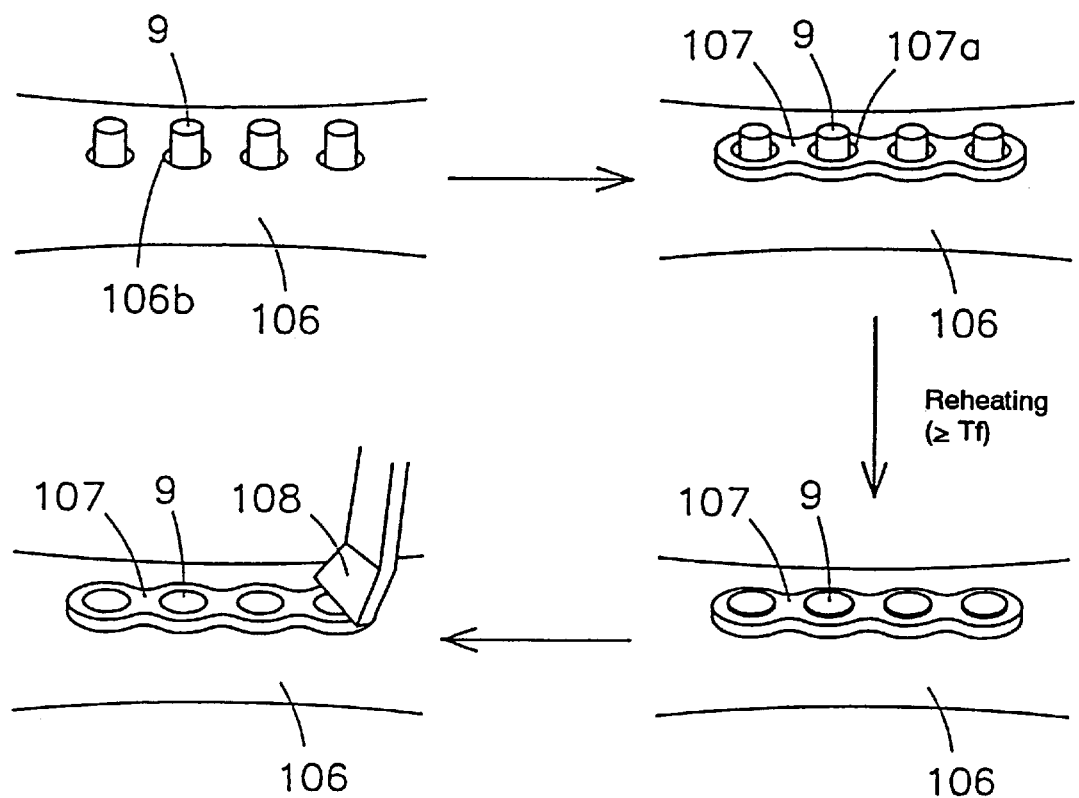
FIG. 19 is a diagram which illustrates how to use the above shape-memory material.

FIG. 18 is a diagram which illustrates a shape-memory biodegradable and absorbable material for fixing a bone plate for fracture fixation(hereinafter referred to simply as "shape-memory material for fixing a bone plate") according to another embodiment of the present invention, while FIG. 19 is a diagram which illustrates how to use the above shape-memory material.

This shape-memory material for fixing a bone plate (9) is obtained by cutting the above-mentioned shape-memory material for bone fixation (8) in the shape of round bars to give tapered pins wherein the diameter of one end is smaller than that of another end. When this shape-memory material (9) is reheated to the above-mentioned deformation temperature (Tf) or above, it is contracted lengthwise but enlarged breadthwise, as shown by the alternate long and short dash line. Thus it is recovered to the shape of short tapered pins having a large diameter.

This shape-memory material (9) in the shape of tapered pines is usable as bone fixation pins as such. It is still preferable to use it in fixing a bone plate (107), as FIG. 19 shows.

Plural holes (106b) having a diameter somewhat larger than that of the shape-memory material (9) are formed in a bone (106). Then the shape-memory material (9) in the form of a tapered pin is inserted into each hole (106b) while making the end with a larger diameter downward. Next, a bone plate (107) provided with holes (107a) as many as the above-mentioned holes (106b) is placed thereon and the top of each tapered pin of the shape-memory material (9) coming out from the surface of the bone (106) is put into each hole (107a) in the bone plate (107). After thus setting the bone plate (107), the shape-memory material (9) is brought into contact with a heat source such as hot water (physiological saline) at the deformation temperature (Tf) or above for the shape-recovery. Thus, the shape-memory material (9) is close to both of the holes (106a) in the bone (106) and the holes (107a) in the bone plate (107) and, therefore, the bone plate (107) is fixed onto the surface of the bone (106). Next, a preheated iron (108) is pressed onto the top of each tapered pin of the shape-memory material (9) coming out from the surface of the bone plate (107) so that the top surface of the shape-memory material (9) and the surface of the bone plate have the same heights. Alternatively, it is also effective that the pin top is preliminarily processed so as to memorize a shape ensuring the fixation of the plate (107).

It is still efficacious to add the above-mentioned bioceramics powders to the shape-memory material for fixing bone plate (9) to thereby accelerate the fixation of the plate and the bone (106).

Figure 20:
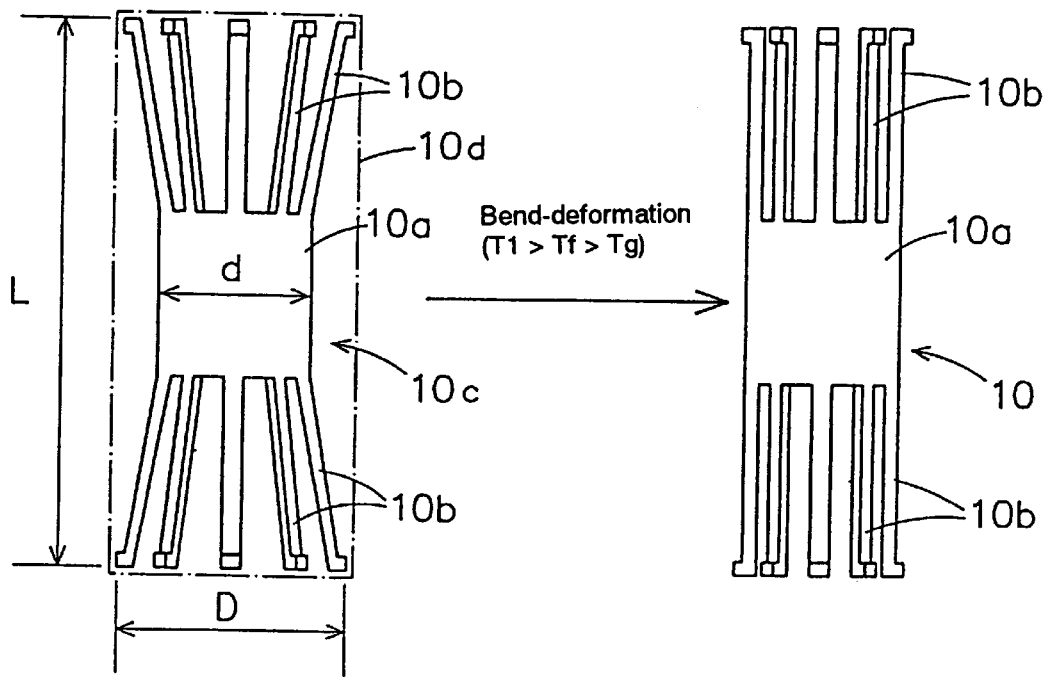
FIG. 20 is a diagram which illustrates a shape-memory material for bone fixation according to another embodiment of the present invention.
Figure 21:
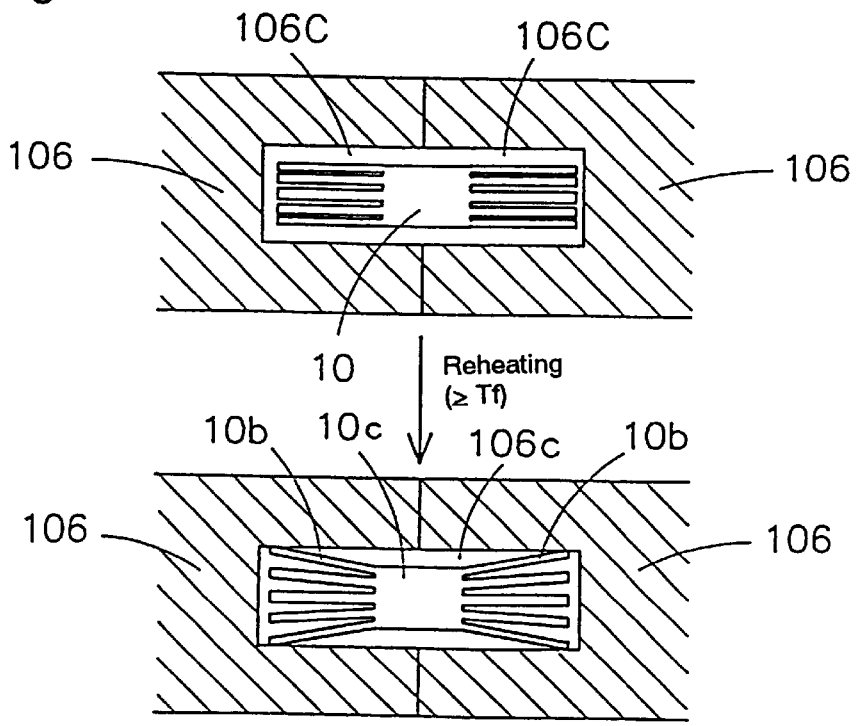
FIG. 21 is a diagram which illustrates how to use the above shape-memory material.

FIG. 20 is a diagram which illustrates a shape-memory material for bone fixation according to another embodiment of the present invention, while FIG. 21 is a diagram which illustrates how to use the above shape-memory material.

This shape-memory material for bone fixation (10) prepared by cutting a cylindrical molded block (10d) made of a lactic acid-based polymer into a molded article (10c) in the shape of a cylinder (10a) provided with two or more (eight in this embodiment) inclined arms (10b) projecting from the peripheries of both ends thereof, deforming this molded article (10c) at a temperature (Tf) higher than the glass transition temperature (Tg) thereof but lower than the crystallization temperature (Tc) thereof (or 100° C. when the molded article has no crystallization temperature) so that each arm (10b) is bent inside at the base in parallel to the axis of the cylinder (1a) and then fixing said molded article to said shape by cooling it as such to a temperature lower than the glass transition temperature.

When this shape-memory material for bone fixation (10) is reheated to the above-mentioned deformation temperature (Tf) or above, it is recovered to the original molded article (10c) wherein each inclined arm (10b) projects outside.

This shape-memory material for bone fixation (10) is used as, for example, a substitute for conventional Herbert screws or the like. As FIG. 21 shows, this shape-memory material (10) is inserted into holes (106c, 106c) which have been formed by drilling the faces of bone fragments (106, 106) to be fixed. Next, it is heated by hot water (physiological saline, etc.) to the above-mentioned deformation temperature (Tf) or above. Thus, the shape-memory material (10) is recovered to the original molded article (10c) wherein each inclined arm (10b) projects outside. Since the tips of each arm (10b) are fixed in contact with the inner faces of both holes (106c, 106c), the bone sections (106, 106) can be easily fixed together.

As FIG. 20 shows, it is preferable that in this shape-memory material for bone fixation (10), each arm (10b) is provided with a click extended outside. Owing to provision of such a click, the inner face of the hole (106c) can well hung up and thus the bone sections (106, 106) can be fixed together more tightly.

It is also desirable to add to this shape-memory material for bone fixation (10) the above-mentioned bioceramics powders so as to accelerate the fixation of the bone (106).

Figure 22:
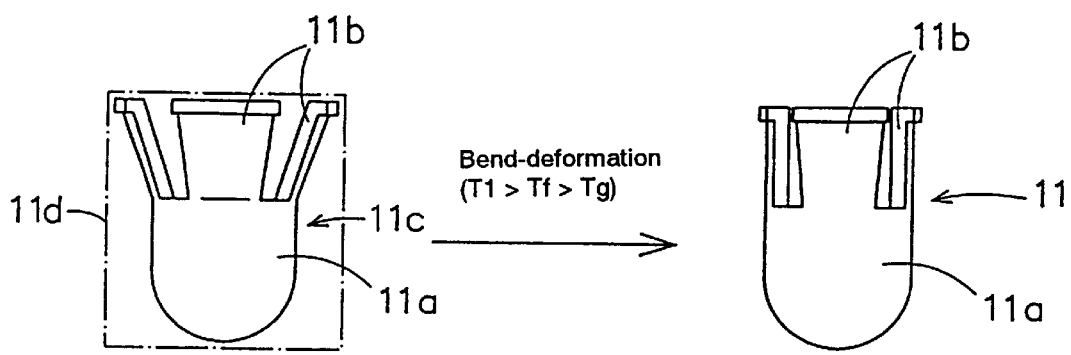
FIG. 22 is a diagram which illustrates a shape-memory material for preventing bone cement in marrow cavity from leakage according to another embodiment of the present invention.
Figure 23:
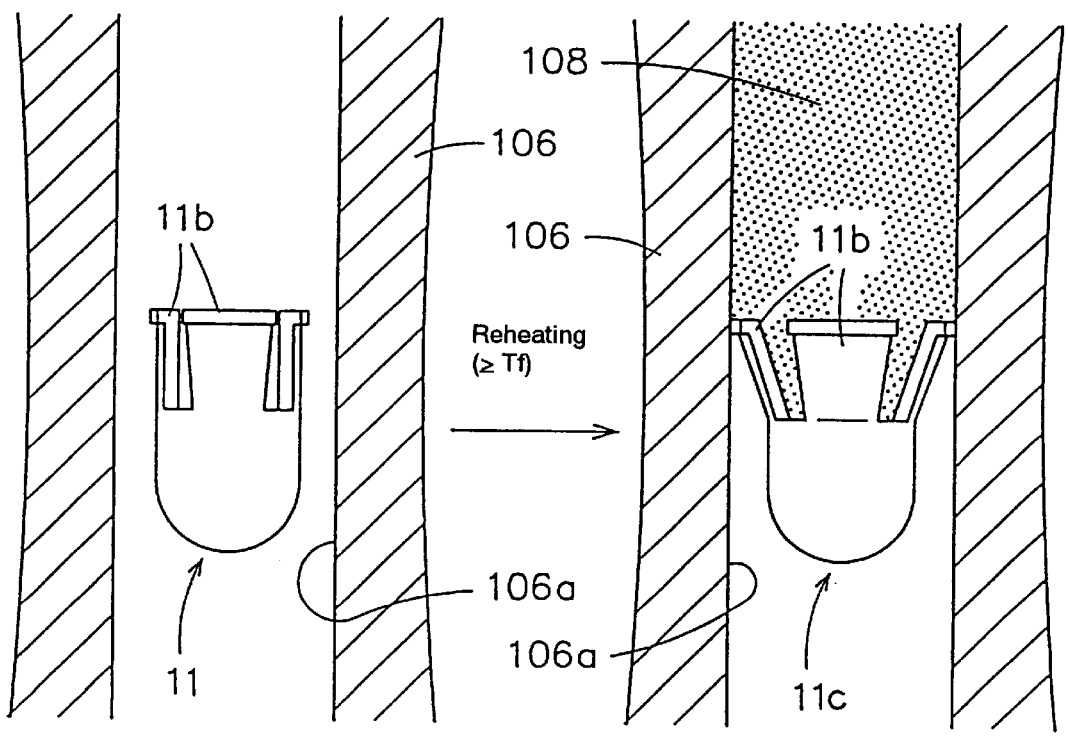
FIG. 23 is a diagram which illustrates how to use the above shape-memory material.

FIG. 22 is a diagram which illustrates a shape-memory biodegradable and absorbable material for preventing bone cement or small pieces of bone in marrow cavity from leakage (hereinafter referred to simply as "shape-memory material for preventing bone cement in marrow cavity from leakage") according to another embodiment of the present invention, while FIG. 23 is a diagram which illustrates how to use the above shape-memory material.

This shape-memory material for preventing bone cement in marrow cavity from leakage (11) prepared by cutting a cylindrical molded block (11d) made of a lactic acid-based polymer to give a molded article (11c) in the shape of a cylindrical plug (11a) having a hemispherical bottom and provided with two or more (four in this embodiment) petal-like inclined projections (11b) extended from the periphery of the upper face thereof, then bending and deforming this molded article (11c) at a temperature higher than the glass transition temperature (Tg) thereof but lower than the crystallization temperature (Tc) thereof (or 100° C. when the molded article has no crystallization temperature) so that each petal-like projection (11b) is bent inside at the base in parallel to the axis of the cylinder (11a) and then fixing said molded article to said shape by cooling it as such to a temperature lower than the glass transition temperature.

When this shape-memory material for bone fixation (11) is reheated to the above-mentioned deformation temperature (Tf) or above, it is quickly recovered to the original molded article (11c) wherein each petal-like projection (11b) is inclined outside. As FIG. 23 shows, this shape-memory material for preventing bone cement in marrow cavity from leakage (11) is inserted into the marrow cavity (106a) of a bone (106) and then reheated by hot water (physiological saline, etc.) to the above-mentioned deformation temperature (Tf) or above. Thus, the shape-memory material (11) is recovered to the original molded article (11c) wherein each petal-like projection (11b) is inclined outside. Thus, the tip of each petal-like projection (11b) is fixed in contact with the inner face of the marrow cavity (106a).

After the shape-memory material (11) is recovered to the original shape and fixed in the marrow cavity (106a), a bone cement (108) is poured from the top of the marrow cavity (106a). Thus, the bone cement (108) is prevented from flowing out downward by each petal-like projection (11b). When an artificial joint stem (not shown) is inserted into the marrow cavity (106a) filled with the bone cement (108), the stem can be surely fixed by the bone cement (108).

It is also desirable to add to this shape-memory material for preventing bone cement in marrow cavity from leakage (11) the above-mentioned bioceramics powders so as to accelerate the fixation of the bone (106). It is also desirable to form a click projecting outside on the tip of each petal-like projection (11b) so that the inner face of the marrow cavity (106a) can well hung up.

The size of each part of the original molded article (11c) may be appropriately determined depending on the size of the marrow cavity into which it is to be inserted.

Figure 24:
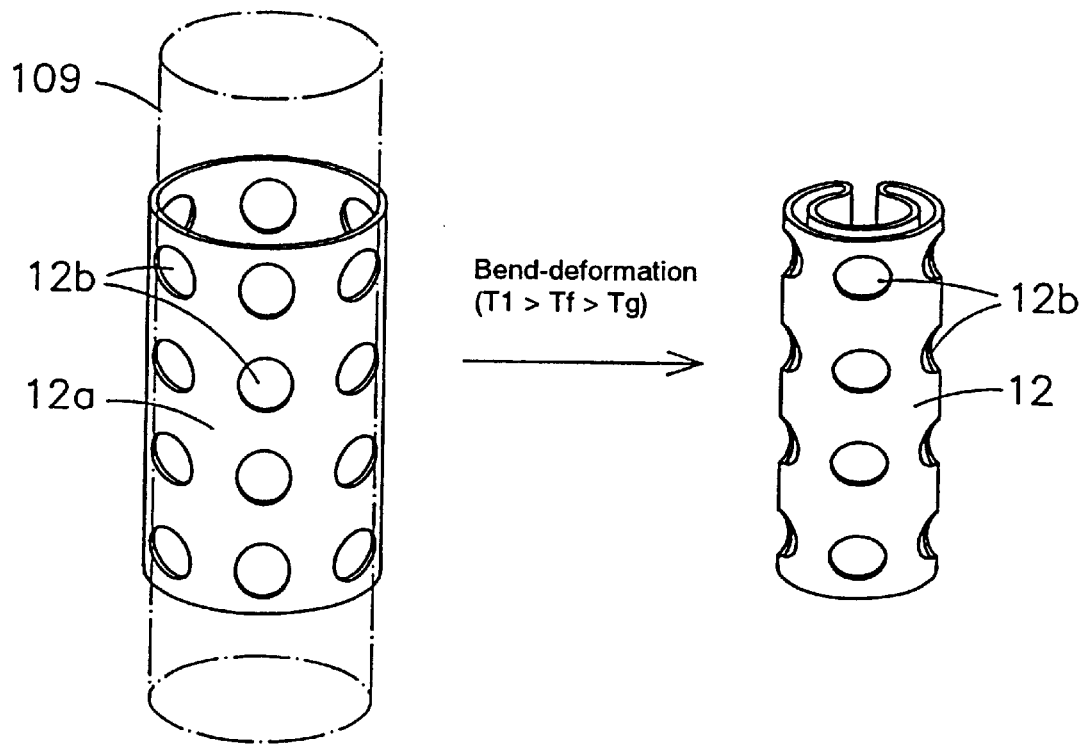
FIG. 24 is a diagram which illustrates a shape-memory material for preventing vascular reconstriction according to another embodiment of the present invention.
Figure 25:
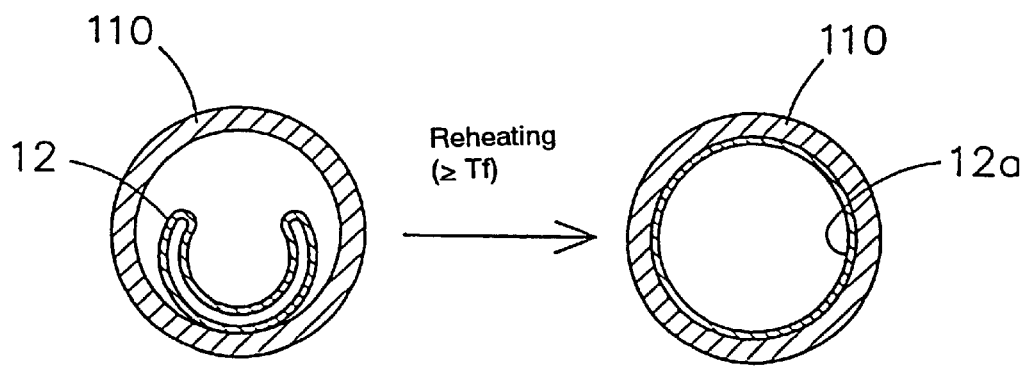
FIG. 25 is a diagram which illustrates how to use the above shape-memory material.

FIG. 24 is a diagram which illustrates a shape-memory biodegradable and absorbable material for preventing vascular reconstriction (hereinafter referred to as "shape-memory material for preventing vascular reconstriction") according to another embodiment of the present invention, while FIG. 25 is a diagram which illustrates how to use the above shape-memory material.

This shape-memory material for preventing vascular reconstriction (12) is prepared by deforming a molded article (12a) made of a lactic acid-based polymer in the shape of a perforated cylinder with a number of pores (12b) into another molded article in the shape of a folded cylinder at a temperature higher than the glass transition temperature (Tg) thereof but lower than the crystallization temperature (Tc) thereof (or 100° C. when the molded article has no crystallization temperature) and then fixing said molded article to said shape by cooling it as such to a temperature lower than the glass transition temperature.

When this shape-memory material for preventing vascular reconstriction (12) is reheated to the above-mentioned deformation temperature (Tf) or above, it is recovered to the original molded article (12a) in the shape of a perforated cylinder. Thus, this shape-memory material for preventing vascular reconstriction (12) is usable as a substitute for a conventional stent for preventing vascular reconstriction. As FIG. 25 shows, the shape-memory material (12) is inserted into a blood vessel (110) such as the coronary artery and then reheated by hot water (physiological saline, etc.) to the above-mentioned deformation temperature (Tf) or above. Thus, the shape-memory material (12) is recovered to the original cylindrical molded article (12a) and extend the inner space of the blood vessel (110), thus preventing vascular reconstriction.

It is also possible that the shape-memory material (12) for preventing vascular reconstriction contains a vascular reconstriction inhibitor which is released at a constant rate from the shape-memory material when it is fixed in the blood vessel (110) as described above. When this shape-memory material (12) contains a drug, it is preferable to prepare the original perforated molded article (12a) in the shape of a cylinder by the following method. This is because, when the molded article (12a) is prepared by melt-extrusion molding, etc., there arises a serious fear that the drug might be deteriorated at the high molding temperature.

That is to say, a lactic acid-based polymer and a drug are dissolved in a solvent to give a polymer solution. Then, the obtained solution is sprayed onto a core (109) and the solvent is vaporized to thereby form a thick cylindrical film around the core (109). Next, a number of holes (12b) are formed on this cylindrical film and then the core is taken off to thereby give a molded article (12a) in the shape of a perforated cylinder.

In this case, a foamed molded article in the shape of a perforated cylinder of an open cell structure can be obtained by dissolving the lactic acid-based polymer and the drug in a mixture of a solvent in which the lactic acid-based polymer is soluble and a non-solvent having a boiling point higher than that of the solvent. When a shape-memory material for preventing vascular reconstriction obtained by bending such a foamed molded article in the shape of a perforated cylinder is fixed in a blood vessel via shape-recovery, there are achieved advantages that hydrolysis proceeds quickly and thus the drug can be released at an increased amount. This is because the foamed molded article has a much larger surface area than non-foamed ones.

In this embodiment, the shape-memory material for preventing vascular reconstriction (12) is obtained by bend-deforming the original molded article (12a) in the shape of a perforated cylinder. Alternatively, it is also possible to subject a net or mesh cylinder to bend-deforming in the same manner. Moreover, it is also possible to produce shape-memory materials for preventing vascular reconstriction by preparing an original molded article in the shape of a large diameter coil (helix) and deforming by constriction (tensile) it into a small diameter coil (helix). It is also possible to produce a shape-memory material for preventing vascular reconstriction by preparing an original molded article in the shape of a coil (helix) and then deforming into the shape of yarns by extension. These materials in the shape of small diameter coils or yarns have an advantage that it can be easily inserted into blood vessels.

Figure 26:
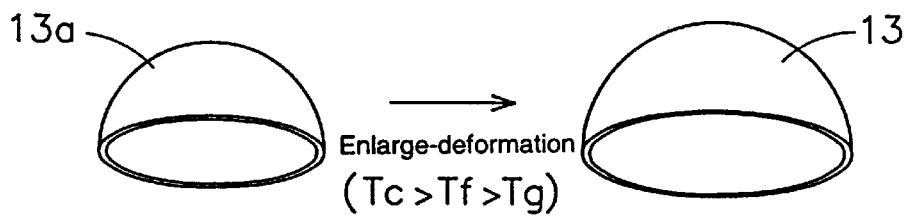
FIGS. 26 and 27 are diagrams which illustrate each a hemisphere cup shape-memory material relating to a linearly located between an artificial hip joint outer head and an acetabular bones according to another embodiments of the present invention.
Figure 27:
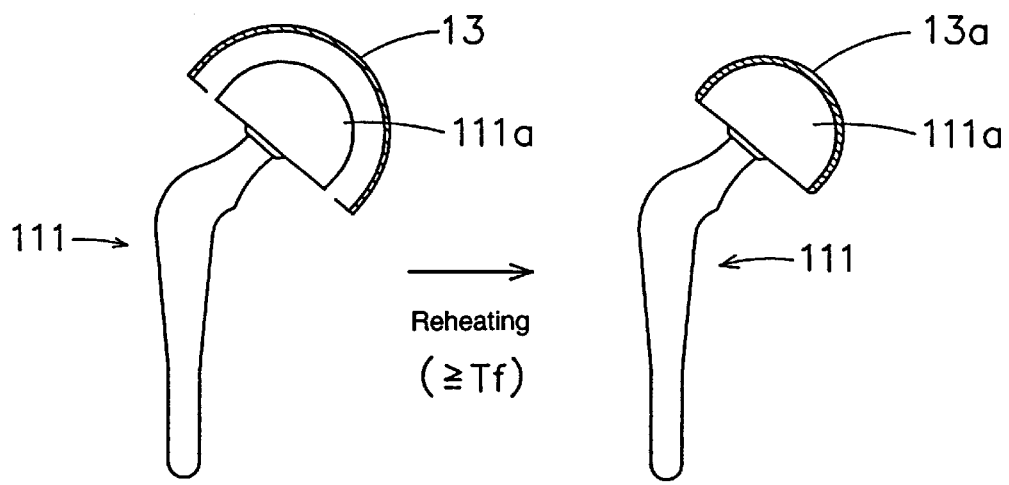
Figure 28:
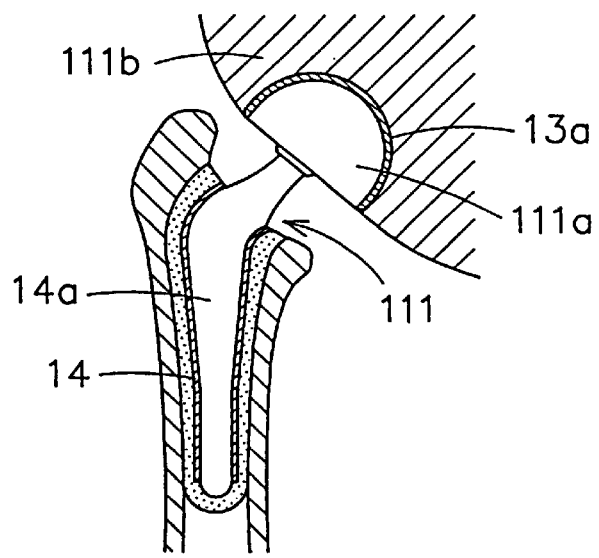
FIG. 28 is a diagram which shows how to use the above shape-memory material.

FIGS. 26 and 27 are diagrams which illustrate each a hemisphere cup shape-memory biodegradable and absorbable material relating to a liner located between an artificial hip joint outer head and an acetabular bone (hereinafter referred to as "hemisphere cup shape-memory material for an artificial hip joint") according to another embodiment of the present invention, while FIG. 28 is a diagram which illustrates how to use the above shape-memory material.

This hemisphere cup shape-memory material for an artificial hip joint (13) is a molded article made of a lactic acid-based polymer preferably containing a bioceramics powder. As FIG. 26 shows, the hemisphere cup shape-memory material (13a), which has the same shape, though smaller, as that of the outer head (111a) of an artificial hip joint (111), is put on a hemisphere mold larger than the outer head (111a) and then heated to a temperature (Tf) higher than the glass transition temperature (Tg) thereof but lower than the crystallization temperature (Tc) thereof (or 100° C. when the molded article has no crystallization temperature) to thereby enlarge and deform, followed by fixing said molded article to said shape by cooling it as such to a temperature lower than the glass transition temperature.

When this hemisphere cup shape-memory material (13) is reheated to the deformation temperature (Tf) or above, it is recovered to the original hemisphere cup molded article (13a) with a smaller size. As FIG. 27 shows, when this hemisphere cup shape-memory material (13) is put on the outer head (111a) and reheated by bringing it into contact with hot water (physiological saline) at the deformation temperature (Tf) or above, this shape-memory material (13) tries to recover the original hemisphere molded material (13a) with a smaller size than the outer head (111a). As a result, it is tightly fixed and closed to the outer head (111a).

As FIG. 28 shows, this hemisphere cup shape-memory material (13) is employed as a spacer for filling up the space between the outer head (111a) and an acetabular bone (111b). Thus, it is preferably a porous hemisphere cup shape-memory material (13). This porous hemisphere cup shape-memory material (13) can be obtained by dissolving a lactic acid-based polymer in a mixture of a solvent in which the lactic acid-based polymer is soluble and a non-solvent having a boiling point higher than that of the solvent, then applying or spraying the obtained solution onto a hemisphere material, and volatilizing the solvent to give a hemisphere cup porous molded article (13a). Next, this hemisphere cup porous molded article (13a) is enlarged by putting on a hemisphere mold larger than the outer head (111a) under the temperature condition as specified above to give a porous hemisphere cup shape-memory material (13).

When this porous hemisphere cup shape-memory material (13) is reheated, it is recovered to the original porous hemisphere cup molded article (13a) and thus can be tightly fixed and closed to the outer head (111a), similar to the above case.

In FIG. 28, the numerical symbol 14 means a porous and cylindrical shape-memory biodegradable and absorbable material prepared by coating an artificial hip joint stem (14a) with the shape-memory material. The porous and cylindrical shape-memory material (14) is formed by the same method as the one employed for preparing the shape-memory material for vascular anastomosis as shown in FIG. 1. Then it is inserted into the stem (14a) and reheated to give the original cylindrical shape-memory material with a small diameter. Thus, it can be closed to the artificial hip joint stem (14a).

There are a great variety of artificial hip joints with various head sizes, surface conditions and forms, as well as stems. By using the coating method as the one employed in the present invention, the shape-memory materials can be commonly applied to various parts (heads, stems, etc.) which correspond to the recovery ratios obtained by heating during the surgical operation. The present invention is also efficaciously applicable to knee joints, etc.

By adding a biologically active bioceramics powder to the outer head, a bone conduction function can be imparted. It is also possible to add a cytokine capable of inducing bone formation.

Thus, it is expected that not only the acetabular bone would be attached to the metallic outer cup having been surface-treated with hydroxyapatite via the porous hemisphere cup shape-memory material but also the postoperative migration (sinking) in the acetabular bone side can be prevented. These phenomena would contribute to the design of novel artificial joints in future.

Thus, the practical uses of the present invention have been described above in detail. However, it is needless to say that the present invention has various uses other than those cited above which are also involved in the scope of the present invention without departing from the spirit of the invention.

To further illustrate the present invention in greater detail, the following Examples will be given.

EXAMPLE 1

DL-Lactide was subjected to ring-opening polymerization to give poly-D,L-lactic acids (PDLLA) having viscosity-average molecular weights of 400,000, 250,000, 150,000, 100,000 and 70,000. These PDLLA were press-molded at 160° C. and 100 kg/cm$^2$ and thus 5 molded PDLLA articles in the shape of round bars (diameter=10.0 mm, length 20 mm) were obtained. The glass transition temperatures of these molded articles all fell within the range of from 50 to 56° C.

Next, these molded articles were each heated to 60° C. and deformed into molded articles in the shape of thin and round bars (diameter=5.8 mm, length=60 mm) by compression molding. Then the resultant molded articles were fixed to the shape by cooling as such at ordinary temperature to give 5 shape-memory biodegradable and absorbable materials with the memory of the original shape of the round bars. The sectional area and length of a shape-memory material were referred respectively to $S_1$ and $L_1$ while the sectional area and length of the original molded article prior to the plastic deformation were referred respectively to $S_0$ and $L_0$. Then each shape-memory material showed a deformation ratio of sectional area $R_S=S_0/S_1=3.0$ and a deformation ratio of length $R_L=L_0/L_1=3.0$.

Subsequently, these shape-memory materials were each immersed in physiological saline at 65° C. and thus recovered to the original shape. After the recovery, the sectional area $S_2$ and length $L_2$ were determined. Thus the recovery ratio of sectional area $[(S_2/S_0)\times100]$ (%) and the recovery ratio of length $[(L_2/L_0)\times100]$ (%) were determined. Table 1 summarizes the results.

TABLE 1

| PDLLA viscosity-average m.w. (× 10$^4$) | Degree of deformation [$R_S = R_L$] | Sectional area recovery ratio [%] | Length recovery ratio [%] |
|---|---|---|---|
| 40 | 3.0 | 97.3 | 96.7 |
| 25 | 3.0 | 97.3 | 97.3 |
| 15 | 3.0 | 97.7 | 98.0 |
| 10 | 3.0 | 98.7 | 98.8 |
| 7 | 3.0 | 99.5 | 99.5 |

Each of the shape-memory materials with various molecular weights was immediately recovered to the original shape by immersing in physiological saline at 65° C. and showed a high recovery ratio of sectional area and a high recovery ratio of length of 96.7% or above. Thus, it was confirmed that each shape-memory material was almost completely recovered to the original (undeformed) shape of round bars.

The shape recovery ratios somewhat depended on molecular weight. This is seemingly because the fluidity of PDLLA was lowered with an increase in molecular weight and thus the internal strain was memorized at the plastic deformation of the original molded articles. However, it was considered that these shape-memory materials could substantially completely recovered to the original shape of round bars.

It is well known that PDLLA obtained by ring-opening polymerization, which are amorphous polymers, are hydrolyzed more quickly in vivo than poly-L-lactic acids (PLLA) which are crystalline polymers. Molded articles of PDLLA are inferior in strength to PLLA having a high strength with orientated molecular chains (crystalline axes). When processed by orientation, etc., PDLLA sometimes undergoes orientation of the amorphous phase and the partially crystalline phase, which results in a somewhat increase in its strength. This phenomenon largely depends on the ratio of the D-isomer to the L-isomer (one of them is used in a higher content), the type of the copolymer, the ratio of the monomers and molecular weight.

The necessary strength, the time of sustaining the same, the absorption rate, etc. of a shape-memory material can be altered by varying these factors. Also, the degradation rate can be regulated by controlling the contents of the lactide monomers in the polymer.

EXAMPLE 2

D-Lactide and L-lactide were polymerized at a weight ratio of 25:75, 40:60 and 50:50 to give 3 PDLLA having a viscosity-average molecular weight of 150,000. These PDLLA were press-molded at 160° C. and 100 kg/cm$^2$ and thus 3 molded PDLLA articles in the shape of round bars (diameter=10.0 mm, length=10 mm) were obtained. The glass transition temperatures of these molded articles all fell within the range of from 50 to 60° C.

Next, these molded articles were each heated to 65° C. and deformed into molded articles in the shape of thin and round bars (diameter=5 mm, length=40 mm) by plastic compression. Then the resultant molded articles were fixed to the shape by cooling as such at ordinary temperature to give 3 shape-memory materials (deformation ratio: $R_S=R_L=4.0$) with the memory of the original shape of the round bars.

Subsequently, these shape-memory materials were each immersed in physiological saline at 70° C., i.e., higher than the one employed in Example 1. After the shape-recovery, the recovery ratios (the recovery ratio of sectional area and the recovery ratio of length) were determined. Table 2 summarizes the results.

TABLE 2

| D-Lactide/<br>L-lactide | Degree of<br>deformation<br>$[R_S = R_L]$ | Sectional area<br>recovery ratio<br>[%] | Length<br>recovery ratio<br>[%] |
| --- | --- | --- | --- |
| 25/75 | 4.0 | 95.5 | 94.5 |
| 40/60 | 4.0 | 96.0 | 95.3 |
| 50/50 | 4.0 | 97.7 | 98.0 |

Each of the shape-memory materials was immediately recovered to the original shape by immersing in physiological saline at 70° C. The shape-recovery ratios depended on the ratio of D-lactide to L-lactide at the polymerization. It was clarified that the sample with the equivalent ratio showed high recovery ratios, i.e., it could be easily recovered to the original (undeformed) shape. The reason therefor is seemingly as follows. In a PDDL containing either D-lactide or L-lactide at a larger ratio, the polymer-constituting molecular chain had parts with consecutive L-lactic acid or D-lactic acid molecules and thus the polymer was slightly crystallized due to the formation of hydrogen bonds in its molecular chain, which caused somewhat decrease in the recovery ratios at 70° C.

EXAMPLE 3

D,L-lactic acid/glycolic acid copolymer (D,L-lactic acid glycolic acid=97.5:2.5) having a viscosity-average molecular weight of 200,000 was press-molded at 180° C. and 100 kg/cm² to give a molded article in the shape of a round bar (diameter=13.0 mm, length=30 mm). The glass transition temperature of this molded article was 51° C.

Next, this molded article was heated to 65° C. and deformed into another molded article in the shape of a thin and round bar (diameter=7.5 mm, length=90 mm) by plastic compression. Then the resultant molded article was fixed to the shape by cooling as such to give a shape-memory material (deformation ratio: $R_S=R_L=3.0$) with the memory of the original shape of the round bar.

Subsequently, this shape-memory material was immersed in physiological saline at 67° C. After the shape-recovery, the recovery ratios (sectional area and length) were determined. Table 3 shows the results.

TABLE 3

| | Degree of<br>deformation<br>$[R_S = R_L]$ | Sectional area<br>recovery ratio<br>[%] | Length<br>recovery ratio<br>[%] |
| --- | --- | --- | --- |
| P (DLLA-GA)<br>90/10 | 3.0 | 99.0 | 98.0 |

This shape-memory material was immediately recovered to the original shape by immersing in physiological saline at 67° C. and showed a high recovery ratio of sectional area and a high recovery ratio of length of 98% or above. Thus, it was almost completely recovered to the original (undeformed) shape of round bars.

EXAMPLE 4

PLLA having a viscosity-average molecular weight of 100,000 was mixed with PDLLA obtained by ring-opening polymerization of D,L-lactide and having a viscosity-average molecular weight of 100,000 at a weight ratio of 70:30. The granules thus obtained were press-molded at 185° C. and 100 kg/cm² to give a molded article in the shape of a round bar (diameter=10 mm, length=20 mm). The apparent glass transition temperature of this molded article was about 60° C.

Next, this molded article was heated to 85° C. and deformed into another molded article in the shape of a thin and round bar (diameter=6.3 mm, length =50 mm) by plastic compression. Then the resultant molded article was fixed to the shape by cooling as such to give a shape-memory material (deformation ratio: $R_S=R_L=2.5$) with the memory of the original shape of the round bar.

Subsequently, this shape-memory material was immersed in physiological saline at 85° C. After the shape-recovery, the recovery ratios (sectional area and length) were determined. Table 4 shows the results.

TABLE 4

| | Degree of<br>deformation<br>$[R_S = R_L]$ | Sectional area<br>recovery ratio<br>[%] | Length<br>recovery ratio<br>[%] |
| --- | --- | --- | --- |
| PLLA/PDLLA<br>70/30 | 2.5 | 94.8 | 98.0 |

This shape-memory material was immediately recovered to the original shape by immersing in physiological saline at 85° C. Although the recovery ratios were somewhat lower than those of the PDLLA of a viscosity-average molecular weight of 100,000 in Example 1, it was almost completely recovered to the original (undeformed) shape of round bars. It was considered that the PLLA moiety in the shape-memory material was slightly crystallized due to the orientation at the plastic deformation in the step of the secondary deformation and thus the recovery ratios were somewhat lower than those of the former one.

EXAMPLE 5

PDLLA obtained by polymerizing D-lactide and L-lactide at a weight ratio of 50:50 and having a viscosity-average molecular weight of 150,000 (the one employed in Example 2) was dissolved in dichloromethane. Then neither calcined nor sintered hydroxyapatite (u-HA)was added to the solution. Subsequently, ethyl alcohol was added thereto under stirring to thereby co-precipitate PDLLA and u-HA. Next, the precipitate was taken up by filtration and completely dried to give two types of PDLLA granules wherein u-HA was uniformly dispersed at a ratio of 40% by weight or 50% by weight.

These granules were press-molded under the same conditions as those employed in Example 2 to give 2 molded articles in the shape of round bars (diameter=10 mm, length=10 mm). Next, these molded articles were heated to 70° C. and deformed into molded articles (deformation ratio: $R_S=R_L=2.8$) in the shape of thin and round bars (diameter= 6.0 mm, length=28 mm) by plastic compression. Then the resultant molded articles were fixed to the shape by cooling as such. Next, these molded articles were cut into tapered shape-memory pins (shape-memory materials) of two types (diameter at one end=1. 2 mm, diameter at another end=1.5 mm, length=25 mm). These tapered pins were immersed in physiological saline at 70° C. and the shape-recovery ratios (sectional area at one end, sectional area at another end, length) were determined. Table 5 summarizes the results.

TABLE 5

|  | Degree of deformation [$R_S = R_L$] | Sectional area recovery ratio at one end [%] | Sectional area recovery ratio at another end [%] | Length recovery ratio [%] |
|---|---|---|---|---|
| u-HA/ PDLLA = 40/60 (wt. %) | 2.8 | 96.1 | 96.1 | 98.2 |
| u-HA/ PDLLA = 50/50 (wt. %) | 2.8 | 93.2 | 92.9 | 95.7 |

Each tapered, shape-memory pin was recovered to the original shape of the thick and short tapered pin immediately after immersing in physiological saline at 70° C. It showed high shape-recovery ratios (about 93% or above in each of the sectional area at one end, sectional area at another end, and length). Thus, it was proved that a shape-memory material can be obtained from a composition of a bioceramics powder with PDLLA.

Next, it was attempted to use the tapered, shape-memory pins made of the composite having an u-HA/PDDLA weight ratio of 50/50 as pins for fixing a bone plate.

As FIG. 19 shows, 4 holes (106b) having a diameter of 2.0 mm were formed in a white rabbit thigh bone (106) by drilling at intervals of 5 mm on a line. Then the tapered, shape-memory pins (9) made of the composition of u-HA/ PDLLA (50/50 by weight) were inserted respectively into the holes (9b) while making the end with a larger diameter downward. Next, a bone fixation plate (107) made of the composite of u-HA/PDLLA (50/50 by weight) and provided with 4 holes having a diameter of 2.2 mm at intervals of 5 mm on a line is placed thereon and the top of each tapered, shape-memory pin (9) coming out from the surface of the bone (106) is put into each hole (107a) in the bone plate (107). After thus setting the bone plate (107), physiological saline at 70° C. was poured onto the tapered, shape-memory pins (9) to thereby recover the pins to the original shape. Thus, the plate (107) was fixed onto the surface of the thigh bone (106). Next, an iron (108) preheated to 150° C. was pressed onto the top of each tapered pin (9) coming out from the surface of the bone plate (107) to make the top of the pin and the surface of the bone plate flat. Thus, the plate (107) was fixed tightly.

Subsequently, an attempt was made to detach the plate fixed onto the thigh bone, i.e., a detaching test. First, the thigh bone onto which the plate had been fixed was placed on a multi-purpose test machine. Then the fixed plate was fastened with a specific fastener and a stress was applied thereon in the direction of drawing the plate. As a result, the plate was not separated from the pins but the plate were broken.

Thus, it was proved that these tapered, shape-memory pins made it possible to easily and surely fix bone plates to bones in vivo. This bone fixation method is highly convenient, compared with the conventional bone fixation method wherein a plate is fixed to a bone fracture site with screws.

EXAMPLE 6

PDLLA having a viscosity-average molecular weight of 250,000 employed in Example 1 was press-molded at 160° C. and 100 kg/cm² to give a molded article in the shape of a round bar (diameter=15 mm, length=50 mm). Next, as shown in FIG. 22, this molded article was cut into a molded article (11c) in the shape of a cylindrical plug (11a) provided with four petal-like inclined projections (11b) extended outside from the periphery of the upper face thereof.

Next, this molded article (11c) was immersed in physiological saline at 60° C. so that each petal-like projection (11b) was bent inside at the base in parallel to the axis of the cylinder (11a) followed by fixing said molded article to said shape by cooling it as such to give a shape-memory material for preventing bone cement in marrow cavity from leakage (11) with the memory of the original (undeformed) shape of the molded article (11c).

This shape-memory material (11) was inserted into the marrow cavity of a white rabbit thigh bone and physiological saline at 60° C. was poured onto the shape-memory material (11) Thus each petal-like projection (11b) of the shape-memory material (11) was recovered to the original (opened-out) shape and thus the shape-memory material (11) was fixed in the marrow cavity.

Subsequently, a bone cement (108) was poured into the marrow cavity which was placed vertically so that the plug was located at the bottom while the cement was located at the top. After hardening the cement, the thigh bone was vertically opened out to confirm the leakage of the cement from the marrow cavity. As a result, it was proved that the bone cement had been hardened in the marrow cavity above the shape-memory material (11) and no leakage occurred. The shape-memory material for preventing bone cement in marrow cavity from leakage (11) was tightly fixed in the marrow cavity.

EXAMPLE 7

A copolymer obtained by polymerizing L-lactide and D,L-lactide at a weight ratio of 95:5 and having a viscosity-average molecular weight of 150,000 was subjected to co-precipitation with neither calcined nor sintered hydroxyapatite (u-HA) in the same manner as the one described in Example 6. After drying, copolymer granules wherein u-HA was uniformly dispersed at a ratio of 40% by weight was obtained.

These granules were press-molded at 185° C. and 100 kg/cm² into a molded article in the shape of a round bar (diameter=10 mm, length=40 mm). This molded article had an apparent glass transition temperature of 62° C.

Next, this molded article was cut into a molded article (10c) (L: 35 mm, d: 3 mm, D: 5 mm) as shown in FIG. 20. Then this molded article (10c) was heated to 85° C. so that each arm (10b) was bent inside at the base in parallel to the axis of the cylinder (10a) followed by fixing said molded article to said shape to give a shape-memory material for bone fixation (10) with the memory of the original shape of the molded article (10c).

Next, a white rabbit tibia was halved to give two bone fragments. Then holes (diameter: 4 mm, depth: 18 mm) was formed on the incised faces of both bone fragments and the shape-memory material for bone fixation (10) was inserted into these holes to thereby fix the bone fragments together. Then physiological saline at 85° C. was poured thereon and thus the shape-memory material for bone fixation (10) was recovered to the original shape. Thus, the bone fragments were tightly fixed together. Although a stress was applied onto the fixed bone sections in the direction of drawing out, the bone fragments were tightly fixed together and the shape-memory material for bone fixation (10) did not fall out.

Thus, it was proved that the shape-memory material for bone fixation (10) could sufficiently fix bone sections.

EXAMPLE 8

Poly-D,L-lactic acid (glass transition temperature: 51° C.) obtained by ring-opening polymerization of DL-lactide and having a viscosity-average molecular weight of 100,000 was extrusion-molded at 180° C. into small diameter pipes (inner diameter=1 mm, outer diameter=5 mm) After cooling, these pipes were sliced to give a molded article in the shape of small diameter rings [inner diameter=1 mm, outer diameter=5mm, length (width)=2 mm]. Next, these rings were enlarged and deformed in an atmosphere at 60° C. into large diameter rings [inner diameter=10 mm, outer diameter=11.5 mm, length (width)=1.5 mm] and then fixed to this shape by cooling to give a shape-memory material with the memory of the original shape of small diameter rings.

When this shape-memory material was immersed in hot water at 70° C., it was immediately recovered to the original shape of small diameter rings in inner diameter, outer diameter and length (width).

EXAMPLE 9

Poly-D,L-lactic acid (glass transition temperature: 50° C.) obtained by ring-opening polymerization of DL-lactide and having a viscosity-average molecular weight of 70,000 was extrusion-molded at 180° C. into small diameter pipes (inner diameter=0.5 mm, outer diameter=3.2 mm). After cooling, these pipes were sliced to give a molded article in the shape of small diameter rings [inner diameter=0.5 mm, outer diameter=3.2 mm, length (width)=1.0 mm]. Next, these rings were enlarged and deformed in an atmosphere at 55° C. into large diameter rings [inner diameter=5.0 mm, outer diameter=6.1 mm, length (width)=0.8 mm] and then fixed to this shape by cooling to give a shape-memory material for vascular ligation with the memory of the original shape of small diameter rings.

This ring for vascular ligation was put into an end of an incised abdominal blood vessel (diameter: about 1 mm) of a white rabbit and then physiological saline at 60° C. was sprayed thereonto. Thus, the ring for vascular ligation was immediately recovered to the original shape of a small diameter ring and ligated the blood vessel, thus completely stanching. Just to make sure, the shape-recovered ring was flattened with a pair of pliers heated to 80° C. so as to completely seal the blood vessel. After 12 weeks, the rabbit was sacrificed and the blood vessel was examined. As a result, the ring almost disappeared but the blood vessel was sealed and the stanching effect was maintained.

EXAMPLE 10

Poly-D,L-lactic acid (glass transition temperature: 52° C.) obtained by ring-opening polymerization of D-lactide and L-lactide (50:50, by weight) and having a viscosity-average molecular weight of 150,000 was extrusion-molded at 180° C. into small diameter pipes (inner diameter=3 mm, outer diameter=5 mm). After cooling, these pipes were sliced to give a molded article in the shape of small diameter rings [inner diameter=3 mm, outer diameter=5 mm, length (width)=1 mm]. Next, these rings were enlarged and deformed in an atmosphere at 60° C. into large diameter rings [inner diameter=15 mm, outer diameter=15.7 mm, length (width)=0.7 mm]. Then these rings were opened-out so as to match with a suture needle to give a hook. Then these opened-out rings were fixed to this shape by cooling to thereby give a shape-memory material for suture having a hook (71) as shown in FIG. 12.

Then, the hook of this shape-memory material for suture (7) was provided with a suture needle with which an incised site (104) of a white rabbit was sewed in several stitches. Thus the incised site (104) was sewed up at several points with the shape-memory material for suture (7), as FIG. 13 shows. Next, physiological saline at 65° C. was sprayed onto the shape-memory material for suture (7). Thus, the shape-memory material for suture (7) at each point was immediately recovered to the original shape of the opened-out, small diameter ring and thus the incised site (104) could be tightly sewed up.

EXAMPLE 11

Poly-D,L-lactic acid (glass transition temperature: 54° C.) obtained by ring-opening polymerization of DL-lactide and having a viscosity-average molecular weight of 250, 000 was dissolved in dichloromethane. Then the obtained solution was applied around a square bar (length=0.5 mm, width=2 mm, height=50 mm) made of polyethylene and then dichloromethane was vaporized to give a molded article in the shape of a flat and square bar (height=20 mm, thickness=0.75 mm, inner length=0.5 mm, width=2 mm).

This molded article was stretched in an atmosphere at 80° C. into a flat and square shape of 40 mm in height and then fixed to this shape by cooling. Further, it was enlarged and deformed in an atmosphere at 60° C. into a flat and square pipe with a large sectional area (height=40 mm, thickness=0.1 mm, inner length=5 mm, width=10 mm) and then fixed to this shape by cooling to give a shape-memory material for tendon fixation with the memory of the original shape of square pipe.

Into the both openings of this shape-memory material, incised tendon sections of a white rabbit foot were inserted. Then physiological saline at 60° C. was sprayed thereonto. Thus, the shape-memory material was immediately recovered to the shape of a flat and square pipe with a small sectional area (inner length=0.5 mm, width=2 mm). Thus, the incised tendon ends were held tightly all around thereby. Moreover, physiological saline at 80° C. was sprayed thereonto. Then, the shape-memory material was recovered to the original shape of a short and square pipe of 20 mm in height and thus the incised tendon ends could come into contact closely.with each other and fixed.

EXAMPLE 12

100 parts by weight of poly-D,L-lactic acid (glass transition temperature: 50° C.) obtained by ring-opening polymerization of DL-lactide and having a viscosity-average molecular weight of 70, 000 and 150 parts by weight of a vascular reconstriction inhibitor tranilast were dissolved in chloroform to give a solution with a solid content of 3% by weight. Then, this solution was sprayed onto a round bar made of polyethylene (diameter 5.0 mm) at a discharge pressure of 8.0 kgf/cm². After vaporizing chloroform, a cylindrical film of 0.3 mm in thickness was formed. Then this cylindrical film was cut into a piece of 15 mm in length and a number of pores (diameter=1.5 mm) were formed on the surface of the film. After taking out the round bar, a perforated molded article (12a) was obtained as shown in FIG. 24. This product weighed 36 mg and contained 21.6 mg of the drug enclosed therein.

As FIG. 24 shows, this perforated cylindrical molded article was folded in flat and wound up to give a pipe (outer diameter: about 1.0 mm) and deformed. Then it was fixed to the shape by quenching to give a wound-up stent (shape-memory material) for preventing vascular reconstriction (12) with the memory of the original shape of perforated cylinder.

Next, the following test was performed in vitro to confirm the shape-memory function of this stent and to measure the drug releasing rate.

Figure 29:
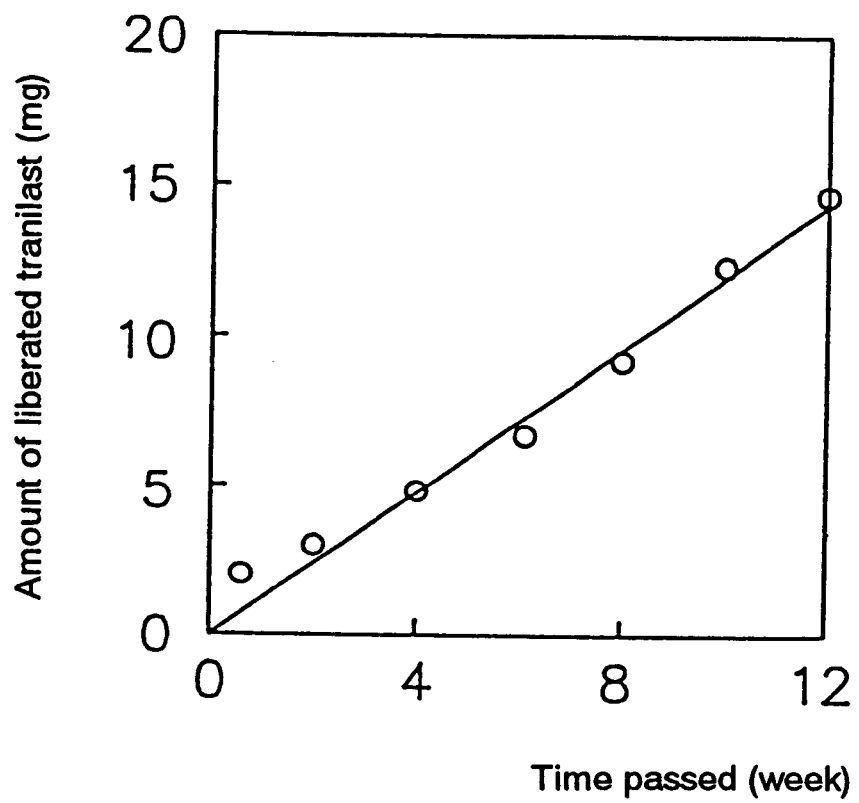
FIG. 29 is a graph which illustrates a relationship between the amount of tranilast released from a shape-memory material for preventing vascular reconstriction and containing tranilast and time.

The stent was inserted into a silicone tube of 4.0 mm in inner diameter and hot water at 60° C. was passed therethrough. With an increase in temperature, the stent was enlarged and recovered to the original cylindrical shape and thus fixed while lining the inner face of the tube due to the pressure applied on the inner wall. Then, it was immersed in a 0.2 M phosphate buffer (pH 7.4) at 37° C. and the amount of tranilast released into the buffer with the degradation of the poly-D,L-lactic acid was determined at constant intervals. As FIG. 29 shows, the drug was released at a constant rate over 12 weeks and it was confirmed that 68% of the tranilast enclosed at the initiation of the test was released during this period. It was also confirmed that a small amount of the poly-D,L-lactic acid still remained.

As described above, it is found out that the shape-memory, biodegradable and absorbable stent can exert excellent functions as a DDS base.

As the above description clearly indicates, when reheated to deformation temperatures, the shape-memory biodegradable and absorbable materials of the present invention make it possible to easily and surely treat vital tissues by ligation, anastomosis, suture, fixation, prevention of vascular reconstriction, etc., i.e., performing treatments of, for example, ligation and anastomosis of incised blood vessels (stanching), suture of incised sites, fixation of incised tendons, bone fixation and prevention of vascular reconstriction. Since these shape-memory materials can be recovered to the original shape by reheating at relatively low temperatures, there is no fear of burn. Moreover, these shape-memory materials never induce halation in MRI or CT and never remain but are degraded and absorbed in vivo, thus achieving favorable effects.

These shape-memory biodegradable and absorbable materials containing bioceramics powders can strongly bind to bone and fix the same in vivo, while those containing drugs can release the drugs at a constant rate and thus serve as DDS bases.

While the invention has been described in detail and with reference to specific embodiments thereof, it will be apparent to one skilled in the art that various changes and modifications can be made therein without departing from the spirit and scope thereof.

This application is based on Japanese patent application No. Hei.-9-139339, filed on May 13, 1997, and incorporated herein by reference.

What is claimed is:

1. A shape-memory biodegradable and absorbable article which comprises a biodegradable and absorbable article prepared by deforming a molded article of a copolymer obtained by ring-opening polymerization of about a 1:1 molar mixture of L-lactide and D-lactide and having a definite original shape into another molded article having another shape at a deformation temperature higher than the glass transition temperature thereof but lower than the crystallization temperature thereof (or 100° C. when the molded article has no crystallization temperature) and then fixing said molded article to the thus deformed shape by cooling it as such to a temperature lower than the glass transition temperature, wherein said molded article can be recovered to the molded article of the original shape by heating it again to said deformation temperature or above.

2. A shape-memory biodegradable and absorbable article which comprises a biodegradable and absorbable article prepared by deforming a molded article of a copolymer obtained by ring-opening polymerization of DL (meso)-lactide and having a definite original shape into another molded article having another shape at a deformation temperature higher than the glass transition temperature thereof but lower than the crystallization temperature thereof (or 100° C. when the molded article has no crystallization temperature) and then fixing said molded article to the thus deformed shape by cooling it as such to a temperature lower than the glass transition temperature, wherein said molded article can be recovered to the molded article of the original shape.

3. A shape-memory biodegradable and absorbable article which comprises a biodegradable and absorbable article prepared by deforming a first molded article of a lactic acid polymer and having a definite original shape into another molded article having another shape at a first deformation temperature higher than the glass transition temperature thereof but lower than the crystallization temperature thereof (or 100° C. when the molded article has no crystallization temperature), then fixing said molded article to the thus deformed shape by cooling it as such to a temperature lower than the glass transition temperature, further deforming said molded article into another molded article having another shape at a second deformation temperature higher than the glass transition temperature but lower than said first deformation temperature and fixing said molded article to the thus deformed shape by cooling it as such to a temperature lower than the glass transition temperature, wherein said molded article can be recovered to the first molded article of the original shape by heating it again to the first deformation temperature or above.

4. A shape biodegradable and absorbable article which comprises a biodegradable and absorbable article prepared by deforming a porous molded article of a lactic acid polymer and having a definite original shape into a substantially non-porous molded article having another shape at a deformation temperature higher than the glass transition temperature thereof but lower than the crystallization temperature thereof (or 100° C. when the molded article has no crystallization temperature) and then fixing said molded article to the thus deformed shape by cooling it as such to a temperature lower than the glass transition temperature, wherein said molded article can be recovered to the porous molded article of the original shape by heating it again to said deformation temperature or above.

5. A shape-memory biodegradable and absorbable article for vascular anastomosis which comprises a molded article of a lactic acid polymer in the shape of large diameter pipes, wherein said molded article can be recovered to a memorized shape of small diameter pipes without applying any external force thereto but by heating to a definite temperature or above.

6. A shape-memory biodegradable and absorbable article for vascular anastomosis which comprises a biodegradable and absorbable material prepared by enlarging and deforming a molded article of a lactic acid polymer in the shape of small diameter pipes into another molded article in the shape of large diameter pipes at a deformation temperature higher than the glass transition temperature thereof but lower than the crystallization temperature thereof (or 100° C. when the molded article has no crystallization temperature) and then fixing said molded article to the shape of large diameter pipes by cooling it as such to a temperature lower than the glass transition temperature, wherein said molded article can be recovered to the molded article in the shape of small diameter pipes by heating it again to said deformation temperature or above.

7. A shape-memory biodegradable and absorbable article for vascular ligation which comprises a molded article of a lactic acid polymer in the shape of large diameter rings, wherein said article can be recovered to a memorized shape of small diameter rings without applying any external force thereto but by heating to a definite temperature or above.

8. A shape-memory biodegradable and absorbable article for vascular ligation which comprises a biodegradable and absorbable material prepared by enlarging and deforming a molded article of a lactic acid polymer in the shape of small diameter rings into another molded article in the shape of large diameter rings at a deformation temperature higher than the glass transition temperature thereof but lower than the crystallization temperature thereof (or 100° C. when the molded article has no crystallization temperature) and then fixing said molded article to the shape of large diameter rings by cooling it as such to a temperature lower than the glass transition temperature followed by cutting into round slices, wherein said molded article can be recovered to the molded article in the shape of small diameter rings cut into round slices by heating it again to said deformation temperature or above.

9. A shape-memory biodegradable and absorbable article for vascular ligation which comprises a biodegradable and absorbable material prepared by enlarging and deforming a molded article of a lactic acid polymer in the shape of small diameter rings into another molded article in the shape of large diameter rings at a deformation temperature higher than the glass transition temperature thereof but lower than the crystallization temperature thereof (or 100° C. when the molded article has no crystallization temperature) and then fixing said molded article to the shape of large diameter rings by cooling it as such to a temperature lower than the glass transition temperature, wherein said molded article can be recovered to the molded article in the shape of small diameter rings by heating it again to said deformation temperature or above.

10. A shape-memory biodegradable and absorbable article for tendon fixation which comprises a biodegradable and absorbable material prepared by enlarging and deforming a molded article of a lactic acid polymer in the shape of almost square small pipes having a flat opening area into another molded article in the shape of almost square large pipes having a large opening area at a deformation temperature higher than the glass transition temperature thereof but lower than the crystallization temperature thereof (or 100° C. when the molded article has no crystallization temperature) and then fixing said molded article to the shape of almost square large pipes having a large opening area by cooling it as such to a temperature lower than the glass transition temperature, wherein said molded article can be recovered to the molded article in the shape of almost square small pipes having a flat opening area by heating it again to said deformation temperature or above.

11. A shape-memory biodegradable and absorbable article for suture which comprises a molded article of a lactic acid polymer in the shape of large diameter opened-out rings, wherein said article can be recovered to an original shape of small diameter rings without applying any external force thereto but by heating to a definite temperature or above.

12. A shape-memory biodegradable and absorbable article for suture which comprises a biodegradable and absorbable material prepared by enlarging and deforming a molded article of a lactic acid polymer in the shape of small diameter rings into another molded article in the shape of large diameter rings at a deformation temperature higher than the glass transition temperature thereof but lower than the crystallization temperature thereof (or 100° C. when the molded article has no crystallization temperature) and then fixing said molded article to the shape of large diameter rings by cooling it as such to a temperature lower than the glass transition temperature followed by opening-out, wherein said molded article can be recovered to the molded article in the shape of small diameter rings having been opened-out by heating it again to said deformation temperature or above.

13. A shape-memory biodegradable and absorbable article for suture which comprises a biodegradable and absorbable material prepared by enlarging and deforming a molded article of a lactic acid polymer in the shape of small diameter rings into another molded article in the shape of large diameter rings at a deformation temperature higher than the glass transition temperature thereof but lower than the crystallization temperature thereof (or 100° C. when the molded article has no crystallization temperature), opening-out said molded article in the shape of large diameter rings, bending a part of the same so as to match with a suture needle, and then fixing said molded article to the shape by cooling it as such to a temperature lower than the glass transition temperature, wherein said molded article can be recovered to the molded article in the shape of small diameter rings having been opened-out by heating it again to said deformation temperature or above.

14. A shape-memory biodegradable and absorbable article for suture which comprises a molded article of a lactic acid polymer in the shape of thin yarns wherein said material can be recovered into the shape of thick yarns without applying any external force thereto but by heating to a definite temperature or above.

15. A shape-memory biodegradable and absorbable article for suture which comprises a biodegradable and absorbable material prepared by drawing and deforming a molded article of a lactic acid polymer in the shape of short, thick yarns into another molded article in the shape of yarns longer and thinner than said ones at a deformation temperature higher than the glass transition temperature thereof but lower than the crystallization temperature thereof (or 100° C. when the molded article has no crystallization temperature) and then fixing said molded article to the shape of thin yarns by cooling it as such to a temperature lower than the glass transition temperature, wherein said molded article can be shortened and thus recovered to the molded article in the shape of short, thick yarns by heating it again to said deformation temperature or above.

16. A shape-memory biodegradable and absorbable article for bone fixation which comprises a molded article of a lactic acid polymer in the shape of thin bars wherein said material can be recovered to an original shape in the shape of thick and round bar without applying any external force thereto but by heating to a definite temperature or above.

17. A shape-memory biodegradable and absorbable article for bone fixation which comprises a biodegradable and absorbable material prepared by deforming a molded article of a lactic acid polymer in the shape of short, thick bars into another molded article in the shape of bars longer and thinner than said ones at a deformation temperature higher than the glass transition temperature thereof but lower than the crystallization temperature thereof (or 100° C. when the molded article has no crystallization temperature) and then fixing said molded article to the shape of thin bars by cooling it as such to a temperature lower than the glass transition temperature, wherein said molded article can be recovered to the molded article in the shape of short, thick bars by heating it again to said deformation temperature or above.

18. The shape-memory biodegradable and absorbable article as claimed in claim 17, wherein said deformed molded article in the shape of long and thin bars is fixed to the shape by cooling and then cut into definite pins.

19. A shape-memory biodegradable and absorbable article for bone fixation which comprises a biodegradable and absorbable material prepared by deforming a molded article of a lactic acid polymer in an original shape of a cylinder provided with two or more inclined arms projecting from the peripheries of both ends thereof at a deformation temperature higher than the glass transition temperature thereof but lower than the crystallization temperature thereof (or 100° C. when the molded article has no crystallization temperature) so that each arm is bent inside at the base in parallel to the axis of the cylinder and then fixing said molded article to said shape by cooling it as such to a temperature lower than the glass transition temperature, wherein said molded article can be recovered to an original shape by heating it again to said deformation temperature or above.

20. A shape-memory biodegradable and absorbable article for preventing bone cement in marrow cavity from leakage which comprises a biodegradable and absorbable material prepared by deforming a molded article of a lactic acid polymer in an original shape of a cylindrical plug having a hemispherical bottom and provided with two or more petal-shaped inclined projections extended from the periphery of the upper face thereof at a deformation temperature higher than the glass transition temperature thereof but lower than the crystallization temperature thereof (or 100° C. when the molded article has no crystallization temperature) so that each petal-shaped projection is bent inside at the base in parallel to the axis of the cylinder and then fixing said molded article to said shape by cooling it as such to a temperature lower than the glass transition temperature, wherein said molded article can be recovered to the original shape by heating it again to said deformation temperature or above.

21. A shape-memory biodegradable and absorbable article for preventing vascular reconstriction which comprises a biodegradable and absorbable material prepared by deforming a molded article of a lactic acid polymer in an original shape of a perforated cylinder with a number of pores or a net or mesh cylinder into another molded article in the shape of a folded cylinder at a deformation temperature higher than the glass transition temperature thereof but lower than the crystallization temperature thereof (or 100° C. when the molded article has no crystallization temperature) and then fixing said molded article to said shape by cooling it as such to a temperature lower than the glass transition temperature, wherein said molded article can be recovered to the original shape by heating it again to said deformation temperature or above.

22. A shape-memory biodegradable and absorbable article for an artificial hip joint comprising a molded article of a copolymer obtained by ring-opening polymerization of about a 1:1 mixture of L-lactide and D-lactide in a hemisphere cup shape, wherein said article can be recovered to a memorized shape of a small hemisphere cup shape without applying any external force thereto but by heating to a definite temperature or above.

23. A shape-memory biodegradable and absorbable article for an artificial hip joint which comprises a biodegradable and absorbable article prepared by enlarging and deforming a molded article of a copolymer obtained by ring-opening polymerization of DL (meso)-lactide in the shape of a small hemisphere cup shape into another molded article in the shape of a large hemisphere cup shape at a deformation temperature higher than the glass transition temperature thereof but lower than the crystallization temperature thereof (or 100° C. when the molded article has no crystallization temperature) and then fixing said molded article to the shape of the large hemisphere cup shape by cooling it as such to a temperature lower than the glass transition temperature, wherein said molded article can be recovered to the molded article in the shape of the small hemisphere cup shape by heating it again to said deformation temperature or above.

24. The shape-memory biodegradable and absorbable material as claimed in claim 1, which further comprises a bioceramics powder.

25. The shape-memory biodegradable and absorbable material as claimed in claim 24, wherein said bioceramics powder is a least one member selected from the group consisting of surface bioactive sintered hydroxyapatite, bioglass for living body use, crystallized glass for living body use, bioabsorbable neither calcined nor sintered hydroxyapatite, dicalcium phosphate, tricalcium phosphate, tetracalcium phosphate, octacalcium phosphate, calcite and diopsite.

26. The shape-memory biodegradable and absorbable material as claimed in claim 1, which further comprises a drug.

27. A shape-memory biodegradable and absorbable article according to claim 5, wherein the lactic acid polymer is a copolymer obtained by ring opening polymerization of about a 1:1 molar mixture of L-lactide and D-lactide or a copolymer obtained by ring-opening polymerization of DL(meso)-lactide.

28. A shape-memory biodegradable and absorbable article according to claim 6, wherein the lactic acid polymer is a copolymer obtained by ring opening polymerization of about a 1:1 molar mixture of L-lactide and D-lactide or a copolymer obtained by ring-opening polymerization of DL(meso)-lactide.

29. A shape-memory biodegradable and absorbable article according to claim 7, wherein the lactic acid polymer is a copolymer obtained by ring opening polymerization of about a 1:1 molar mixture of L-lactide and D-lactide or a copolymer obtained by ring-opening polymerization of DL(meso)-lactide.

30. A shape-memory biodegradable and absorbable article according to claim 8, wherein the lactic acid polymer is a copolymer obtained by ring opening polymerization of about a 1:1 molar mixture of L-lactide and D-lactide or a copolymer obtained by ring-opening polymerization of DL(meso)-lactide.

31. A shape-memory biodegradable and absorbable article according to claim 9, wherein the lactic acid polymer is a copolymer obtained by ring opening polymerization of about a 1:1 molar mixture of L-lactide and D-lactide or a copolymer obtained by ring-opening polymerization of DL(meso)-lactide.

32. A shape-memory biodegradable and absorbable article according to claim 10, wherein the lactic acid polymer is a copolymer obtained by ring opening polymerization of about a 1:1 molar mixture of L-lactide and D-lactide or a copolymer obtained by ring-opening polymerization of DL(meso)-lactide.

33. A shape-memory biodegradable and absorbable article according to claim 11, wherein the lactic acid polymer is a copolymer obtained by ring opening polymerization of about a 1:1 molar mixture of L-lactide and D-lactide or a copolymer obtained by ring-opening polymerization of DL(meso)-lactide.

34. A shape-memory biodegradable and absorbable article according to claim 12, wherein the lactic acid polymer is a copolymer obtained by ring opening polymerization of about a 1:1 molar mixture of L-lactide and D-lactide or a copolymer obtained by ring-opening polymerization of DL(meso)-lactide.

35. A shape-memory biodegradable and absorbable article according to claim 13, wherein the lactic acid polymer is a copolymer obtained by ring opening polymerization of about a 1:1 molar mixture of L-lactide and D-lactide or a copolymer obtained by ring-opening polymerization of DL(meso)-lactide.

36. A shape-memory biodegradable and absorbable article according to claim 14, wherein the lactic acid polymer is a copolymer obtained by ring opening polymerization of about a 1:1 molar mixture of L-lactide and D-lactide or a copolymer obtained by ring-opening polymerization of DL(meso)-lactide.

37. A shape-memory biodegradable and absorbable article according to claim 15, wherein the lactic acid polymer is a copolymer obtained by ring opening polymerization of about a 1:1 molar mixture of L-lactide and D-lactide or a copolymer obtained by ring-opening polymerization of DL(meso)-lactide.

38. A shape-memory biodegradable and absorbable article according to claim 16, wherein the lactic acid polymer is a copolymer obtained by ring opening polymerization of about a 1:1 molar mixture of L-lactide and D-lactide or a copolymer obtained by ring-opening polymerization of DL(meso)-lactide.

39. A shape-memory biodegradable and absorbable article according to claim 17, wherein the lactic acid polymer is a copolymer obtained by ring opening polymerization of about a 1:1 molar mixture of L-lactide and D-lactide or a copolymer obtained by ring-opening polymerization of DL(meso)-lactide.

40. A shape-memory biodegradable and absorbable article according to claim 18, wherein the lactic acid polymer is a copolymer obtained by ring opening polymerization of about a 1:1 molar mixture of L-lactide and D-lactide or a copolymer obtained by ring-opening polymerization of DL(meso)-lactide.

41. A shape-memory biodegradable and absorbable article according to claim 19, wherein the lactic acid polymer is a copolymer obtained by ring opening polymerization of about a 1:1 molar mixture of L-lactide and D-lactide or a copolymer obtained by ring-opening polymerization of DL(meso)-lactide.

42. A shape-memory biodegradable and absorbable article according to claim 20, wherein the lactic acid polymer is a copolymer obtained by ring opening polymerization of about a 1:1 molar mixture of L-lactide and D-lactide or a copolymer obtained by ring-opening polymerization of DL(meso)-lactide.

43. A shape-memory biodegradable and absorbable article according to claim 21, wherein the lactic acid polymer is a copolymer obtained by ring opening polymerization of about a 1:1 molar mixture of L-lactide and D-lactide or a copolymer obtained by ring-opening polymerization of DL(meso)-lactide.

44. A shape-memory biodegradable and absorbable article for an artificial hip joint comprising a molded article of a lactic acid polymer in a hemisphere cup shape, wherein said article can be recovered to a memorized shape of a small hemisphere cup shape without applying any external force thereto but by heating to a definite temperature or above.

45. The shape-memory article according to claim 44, wherein the lactic acid polymer is a copolymer obtained by ring-opening polymerization of DL(meso)-lactide.

46. A shape-memory biodegradable and absorbable article for hip joint which comprises a biodegradable and absorbable article prepared by enlarging and deforming a molded article of a lactic acid polymer in the shape of a small hemisphere cup shape into another molded article in the shape of a large hemisphere cup shape at a deformation temperature higher than the glass transition temperature thereof but lower than the crystallization temperature thereof (or 100° C. when the molded article has no crystallization temperature) and then fixing said molded article to the shape of the large hemisphere cup shape by cooling it as such to a temperature lower than the glass transition temperature, wherein said molded article can be recovered to the molded article in the shape of the small hemisphere cup shape by heating it again to said deformation temperature or above.

47. The shape memory article according to claim 46, wherein the lactic acid polymer is a copolymer obtained by ring-opening polymerization of about a 1:1 mixture of L-lactide and D-lactide.

\* \* \* \* \*